United States Patent
Patil et al.

(10) Patent No.: US 12,333,677 B2
(45) Date of Patent: Jun. 17, 2025

(54) METHODS AND SYSTEMS FOR SUPER-RESOLUTION WITH PROGRESSIVE SUB-VOXEL UP-SAMPLING

(71) Applicant: GE Precision Healthcare LLC, Wauwatosa, WI (US)

(72) Inventors: Rohan Keshav Patil, Karnataka (IN); Sudhanya Chatterjee, Karnataka (IN)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 390 days.

(21) Appl. No.: 17/810,271

(22) Filed: Jun. 30, 2022

(65) Prior Publication Data
US 2024/0005451 A1    Jan. 4, 2024

(51) Int. Cl.
G06T 3/4076    (2024.01)
G06T 3/4046    (2024.01)
G16H 30/40    (2018.01)

(52) U.S. Cl.
CPC .......... G06T 3/4076 (2013.01); G06T 3/4046 (2013.01); G16H 30/40 (2018.01)

(58) Field of Classification Search
CPC ...... G06T 3/4076; G06T 3/4046; G16H 30/40
See application file for complete search history.

(56) References Cited

U.S. PATENT DOCUMENTS

| | | | |
|---|---|---|---|
| 10,304,193 B1 * | 5/2019 | Wang | G06V 10/764 |
| 2011/0292287 A1 | 12/2011 | Washington | |
| 2020/0104695 A1 * | 4/2020 | Laaksonen | G16H 50/70 |
| 2020/0105394 A1 * | 4/2020 | Laaksonen | A61N 5/1064 |
| 2020/0105399 A1 * | 4/2020 | Laaksonen | G06N 3/08 |
| 2020/0408864 A1 | 12/2020 | Mailhe | |
| 2022/0058438 A1 | 2/2022 | Prince | |
| 2022/0114702 A1 * | 4/2022 | Liu | H04N 23/951 |
| 2023/0196662 A1 * | 6/2023 | Kaskela | G06N 3/0464 345/611 |

(Continued)

OTHER PUBLICATIONS

International Application No. PCT/US2023/069435 filed Jun. 29, 2023—International Search Report and Written Opinion issued on Nov. 20, 2023; 14 pages.

(Continued)

*Primary Examiner* — David Bilodeau
(74) *Attorney, Agent, or Firm* — McCoy Russell LLP

(57) ABSTRACT

Various methods and systems are provided for generating super-resolution images. In one embodiment, a method comprises: progressively up-sampling an input image to generate a super-resolution output image by: generating N intermediate images based on the input image, where N is equal to at least one, including a first intermediate image by providing the input image to a deep neural network, where a resolution of the first intermediate image is a multiple of a resolution of the input image, higher than the resolution of the input image, and can be any positive real value and not necessarily an integer value; generating the super-resolution output image based on the N intermediate images, the super-resolution output image having a resolution higher than a respective resolution of each intermediate image of the N intermediate images and the resolution of the input image; and displaying the super-resolution output image via a display device.

20 Claims, 16 Drawing Sheets

(56) References Cited

U.S. PATENT DOCUMENTS

2023/0206394 A1* 6/2023 Janis ..................... G06T 3/4053
 345/595
2024/0185386 A1* 6/2024 Pan ....................... G06T 3/4046

OTHER PUBLICATIONS

Lim, B. et al., "Enhanced Deep Residual Networks for Single Image Super-Resolution," Proceedings of the IEEE Conference on Computer Vision and Pattern Recognition (CVPR) Workshops, Jul. 21, 2017, Honolulu, Hawaii, 9 pages.

Lai, W. et al., "Deep Laplacian Pyramid Networks for Fast and Accurate Super-Resolution," Proceedings of the IEEE Conference on Computer Vision and Pattern Recognition (CVPR) Workshops, Jul. 21, 2017, Honolulu, Hawaii, 9 pages.

Wang, Y. et al., "A Fully Progressive Approach to Single-Image Super-Resolution," Proceedings of the IEEE Conference on Computer Vision and Pattern Recognition (CVPR) Workshops, Jun. 18, 2018, Salt Lake City, Utah, 10 pages.

Zhang, Y. et al., "Image Super-Resolution Using Very Deep Residual Channel Attention Networks," Proceedings of the European Conference on Computer Vision (ECCV), Sep. 8, 2018, Munich, Germany, 16 pages.

Hu, X. et al., "Meta-SR: A Magnification-Arbitrary Network for Super-Resolution," Proceedings of the IEEE/CVF Conference on Computer Vision and Pattern Recognition (CVPR), Jun. 16, 2019, Long Beach, California, 10 pages.

Xue, X. et al., "Progressive Sub-Band Residual Learning Network for MR Image Super Resolution," IEEE Jounral of Biomedical and Health Informatics, vol. 24, No. 2, Feb. 2020, 10 pages.

Schocher, A. et al., "From Discrete to Continuous Convolution Layers," arXiv Cornell University Website, Available Online at https://arxiv.org/pdf/2006.11120.pdf, Available as Early as Jun. 19, 2020, 13 pages.

Lyu, Q. et al., "Multi-Contrast Super-Resolution MRI Through a Progressive Network," IEEE Transactions on Medical Imaging, vol. 39, No. 9, Sep. 2020, 31 pages.

Zhu, J. et al., "MIASSR: An Approach for Medical Image Arbitrary Scale Super-Resolution," arXiv Cornell University Website, Available Online at https://arxiv.org/pdf/2105.10738.pdf, Available as Early as May 22, 2021, 19 pages.

Wang, L. et al., "Learning a Single Network for Scale-Arbitrary Super-Resolution," Proceedings of the IEEE/CVF International Conference on Computer Vision (ICCV), Oct. 11, 2021, Virtual Conference, 10 pages.

* cited by examiner

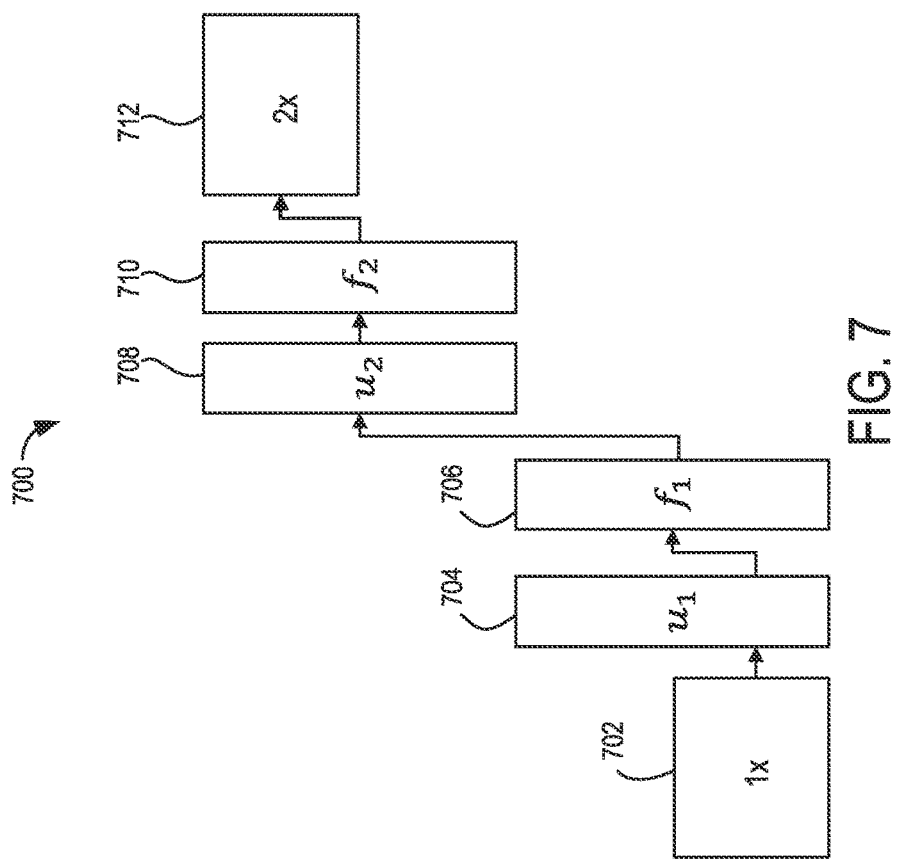
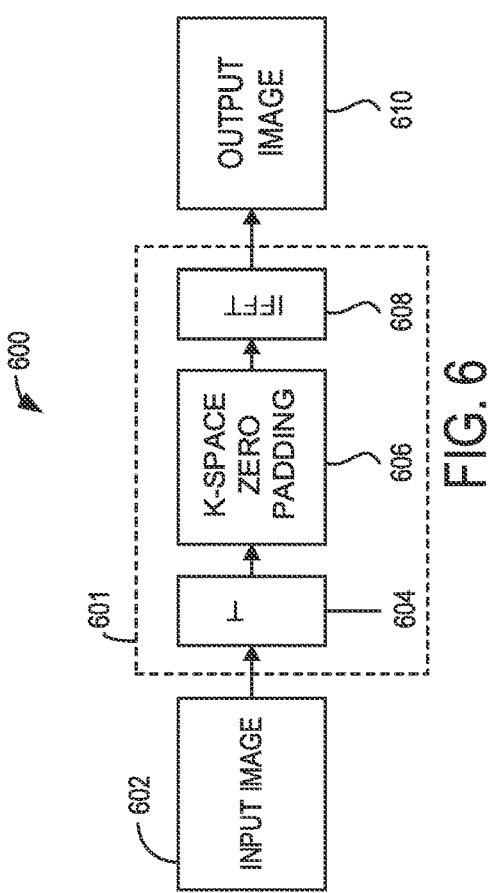

METHODS AND SYSTEMS FOR SUPER-RESOLUTION WITH PROGRESSIVE SUB-VOXEL UP-SAMPLING

FIELD

Embodiments of the subject matter disclosed herein relate to image up-sampling, and, in particular, to up-sampling of medical images.

BACKGROUND

Image quality assessment is often performed alongside image feature identification. In the environment of medical imaging, a technician or other personnel often assesses medical image quality as well as anatomical features shown by the medical images to inform decisions for patient treatment, diagnosis, etc. Image assessment often includes analysis of image resolution, clarity, sharpness, etc., and identification of anatomical features may be based on the type of imaging performed.

Some images may include voxel image data, such as medical images acquired by a magnetic resonance imaging (MRI) modality. Images acquired via a medical imaging modality such as MRI often have a fixed image resolution, such as a fixed number of voxels, selected at the time of acquisition of the images. A speed of the image acquisition may be based on the selected resolution, with larger image resolutions having larger numbers of voxels being associated with larger acquisition times. Because movement of the imaged subject during acquisition of the images may result in image artifacts and/or aberrations, the technician often selects imaging parameters to balance acquisition time with image quality and resolution. However, identification of anatomical features within the images for patient treatment, diagnosis, etc. is often easier with larger resolution images. Therefore, it is generally desired to perform such assessment using images having larger image resolutions.

BRIEF DESCRIPTION

In one embodiment, a method comprises: progressively up-sampling an input image to generate a super-resolution output image by: generating N intermediate images based on the input image, where N is equal to at least one, including a first intermediate image by providing the input image to a deep neural network, where a resolution of the first intermediate image is a multiple of a resolution of the input image, higher than the resolution of the input image, and can be any positive real value and not necessarily an integer value; generating the super-resolution output image based on the N intermediate images, the super-resolution output image having a resolution higher than a respective resolution of each intermediate image of the N intermediate images and the resolution of the input image; and displaying the super-resolution output image via a display device and/or storing the super-resolution output image to a computer memory. Any number of intermediate steps may be performed to reach the final super-resolution image, and all of the intermediate image resolutions may be stored in memory.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below:

FIG. 6 shows a block diagram illustrating a modality-specific sub-voxel up-sampling module.

FIG. 7 shows a block diagram illustrating a sequence of modality-specific progressive up-sampling of an input image to a super-resolution output image using one intermediate image.

DETAILED DESCRIPTION

Figure 1:
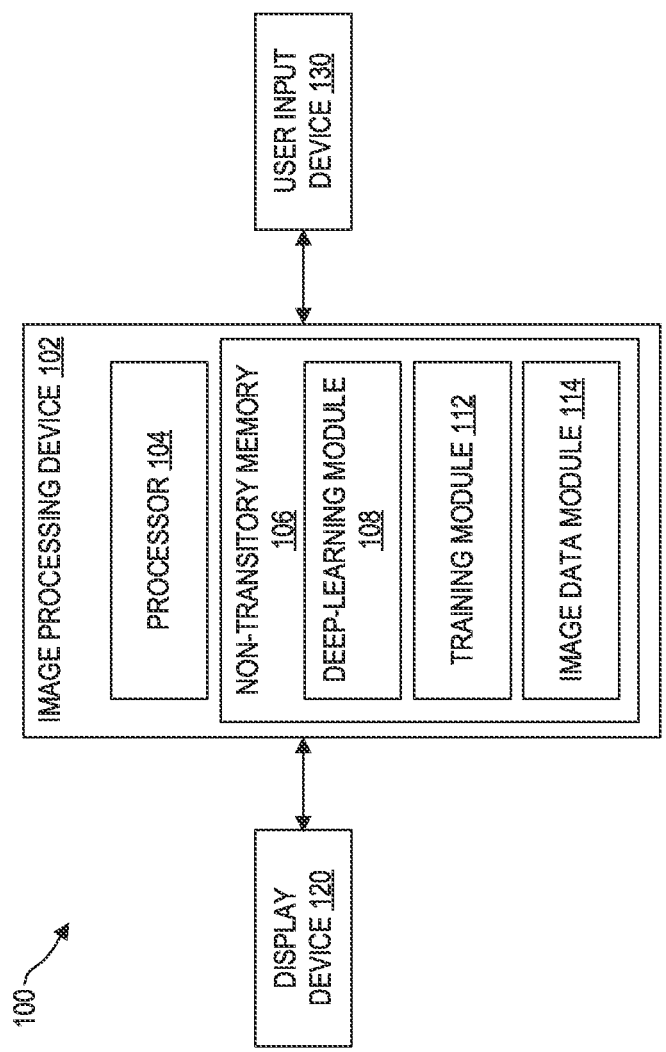
FIG. 1 shows a block diagram of an image processing system according to an embodiment.

The following description relates to various embodiments for progressive sub-voxel up-sampling of input images to generate super-resolution output images.

Generating a super-resolution image is the process of increasing a resolution and clarity of an image. According to the methods described herein, generating a super-resolution output image may include processing an input image and one or more intermediate images via an up-sampling model, such as a deep learning network and/or a convolutional neural network. For example, an input image having a lower, first resolution may be progressively scaled to a super-resolution output image having a higher, second resolution by generating at least one intermediate image with a resolution that is a multiple of the resolution of the input image, higher than the resolution of the input image, and can be any positive real value and not necessarily an integer value (e.g., a non-integer multiple of the resolution of the input image). A first intermediate image may be generated from the input image by scaling the input image via the machine-learning model, and the first intermediate image may be scaled to a second intermediate image or the super-resolution output image via the machine-learning model. By progressively scaling the input image to the super-resolution output image via the machine-learning model and the one or more intermediate images, a clarity of the super-resolution output image may be increased relative to output images scaled directly from the input images without the one or more intermediate images. As a result, an interpretability of the super-resolution output image may be increased for analysis of the image (e.g., for patient diagnosis, treatment, etc.).

The number of intermediate images generated during the progressive scaling of the input image to the super-resolution output image may be selected by the user (e.g., the technician). The progressive scaling of the input image to the super-resolution output image may be referred to herein as progressive sub-voxel up-sampling. As one example, the user may select the scaling of the super-resolution output image such that the resolution of the super-resolution output image is twice the resolution of the input image (e.g., the scale of the super-resolution output image may be selected to be 2×, where the scale of the input image is 1×).

The user may additionally input a number of intermediate scaling stages to be used in the generation of the super-resolution output image from the input image. For example, the user may input a selection of three intermediate stages, resulting in generation of a first intermediate image with a scale of 1.25×, a second intermediate image with a scale of 1.5×, and a third intermediate image with a scale of 1.75×. In this example, the resolution of the first intermediate image is equal to the resolution of the input image multiplied by 1.25, the resolution of the second intermediate image is equal to the resolution of the input image multiplied by 1.5, and the resolution of the third intermediate image is equal to the resolution of the input image multiplied by 1.75 (e.g., the first intermediate image includes the number of voxels included by the input image multiplied by 1.25, the second intermediate image includes the number of voxels included by the input image multiplied by 1.5, and the third intermediate image includes the number of voxels included by the input image multiplied by 1.75).

Image scale, as described herein, refers to a voxel resolution (e.g., number of voxels) included by an image relative to other images. For example, an input image may have a scale of 1× and an intermediate image may have a scale of 1.5×, where the intermediate image includes a number of voxels equal to the number of voxels included by the input image multiplied by 1.5.

The input image, the super-resolution output image, and each of the intermediate images may be displayed together for analysis by the user, as described above. By displaying the intermediate images along with the input image and the super-resolution output image, the user may more easily evaluate the up-sampling of the input image to the super-resolution output image and compare the features shown by the super-resolution output image to the features shown by the input image. As a result, the features shown by the images (e.g., anatomical features of the patient) may be more easily identified by the user, which may increase a speed of the analysis of the images and/or increase a confidence of patient diagnosis.

In some embodiments the up-sampling of the input image and the one or more intermediate images may include modality-specific adjustments to the image data. For example, an input image acquired via the magnetic resonance imaging (MRI) modality may be progressively up-sampled to a resulting super-resolution output image using a machine-learning model trained on MRI images. Progressive up-sampling of an input image acquired via MRI using the machine-learning model trained on MRI images may increase a clarity of the features shown in the resulting super-resolution output image.

Referring to FIG. 1, image processing system 100 is shown according to an embodiment. In some embodiments, the image processing system 100 may be incorporated into an imaging system, such as a medical imaging system. In some embodiments, at least a portion of image processing system 100 is disposed at a device (e.g., edge device, server, etc.) communicably coupled to a medical imaging system via wired and/or wireless connections. In some embodiments, at least a portion of the image processing system 100 is disposed at a device (e.g., a workstation), located remote from a medical imaging system, which is configured to receive images from the medical imaging system or from a storage device configured to store images acquired by the medical imaging system. Image processing system 100 may comprise image processing device 102, user input device 130, and display device 120. In some embodiments, image processing device 102 may be communicably coupled to a picture archiving and communication system (PACS), and may receive images from, and/or send images to, the PACS.

Image processing device 102 includes a processor 104 configured to execute machine readable instructions stored in non-transitory memory 106. Processor 104 may be referred to herein as a controller and/or electronic controller. Processor 104 may be single core or multi-core, and the programs executed thereon may be configured for parallel or distributed processing. In some embodiments, the processor 104 may optionally include individual components that are distributed throughout two or more devices, which may be remotely located and/or configured for coordinated processing. In some embodiments, one or more aspects of the processor 104 may be virtualized and executed by remotely-accessible networked computing devices configured in a cloud computing configuration.

Non-transitory memory 106 may store deep-learning module 108, training module 112, and image data 114. Deep-learning module 108 may be a convolutional neural network module, in some embodiments. For example, the deep-learning module 108 may include one or more trained or untrained convolutional neural networks, comprising a plurality of convolution layers, weights and biases, activation functions, pooling functions, and instructions for implementing the one or more convolutional neural networks to generate super-resolution output images from input images according to the methods described herein. For example, deep-learning module 108 may comprise convolutional neural networks (CNNs) and may perform progressive sub-voxel up-sampling of an input medical image to a super-resolution output medical image using said one or more CNNs by executing one more operations of the method illustrated by the flowcharts of FIG. 16.

Deep-learning module 108 may include various metadata pertaining to the trained and/or un-trained CNNs. In some embodiments, the CNN metadata may include an indication of the training data used to train a CNN, a training method employed to train a CNN, and an accuracy/validation score of a trained CNN. In some embodiments, deep-learning module 108 may include metadata indicating the type(s) of ROI and/or imaging modalities for which the CNN is trained, a size of input image which the trained CNN is configured to process, and a type of anatomy, and/or a type of imaging modality, to which the trained CNN may be applied. In some embodiments, the deep-learning module 108 is not disposed at the image processing device 102, but is disposed at a remote device communicably coupled with image processing device 102 via wired or wireless connection.

Non-transitory memory 106 may further include training module 112, which comprises machine executable instructions for training one or more of the CNNs stored in deep-learning module 108. In some embodiments, the training module 112 is not disposed at the image processing device 102, but is disposed remotely, and may be communicably coupled with image processing device 102. In some embodiments, training module 112 may include instructions for training a CNN to perform one or more of the operations of the methods described herein, such as the method illustrated by the flowchart of FIG. 16 and discussed in more detail below. In one embodiment, the training module 112 may include gradient descent algorithms, loss/cost functions, and machine executable rules for generating and/or selecting training data for use in training CNNs.

Non-transitory memory 106 may further include image data module 114, comprising images/imaging data acquired by one or more imaging devices, which may include (but is not limited to) ultrasound images, MRI images, positron emission tomography (PET) images, X-ray images, computed tomography (CT) images, etc. In some embodiments, the images stored in image data module 114 may comprise medical images from various imaging modalities or from various makes/models of medical imaging devices. The images may include various views of anatomical regions of one or more patients. In some embodiments, medical images stored in image data module 114 may include information identifying an imaging modality and/or an imaging device (e.g., model and manufacturer of an imaging device) by which the medical image was acquired. In some embodiments, images stored in image data module 114 may include metadata indicating one or more acquisition parameters used to acquire said images. In one example, metadata for the images may be stored in DICOM headers of the images. In some embodiments, image data module 114 may comprise x-ray images acquired by an x-ray device, MR images captured by an MRI system, CT images captured by a CT imaging system, PET images captured by a PET system, and/or one or more additional types of medical images.

In some embodiments, the non-transitory memory 106 may include components disposed at two or more devices, which may be remotely located and/or configured for coordinated processing. In some embodiments, one or more aspects of the non-transitory memory 106 may include remotely-accessible networked storage devices configured in a cloud computing configuration.

Image processing system 100 may further include user input device 130. User input device 130 may comprise one or more of a touchscreen, a keyboard, a mouse, a trackpad, a motion sensing camera, or other device configured to enable a user to interact with and manipulate data within image processing system 100. In some embodiments, user input device 130 enables a user to select one or more input images for progressive sub-voxel up-sampling of the input images to super-resolution output images according to the methods described herein.

Display device 120 may include one or more display devices utilizing virtually any type of technology. In some embodiments, display device 120 may comprise a computer monitor, a touchscreen, a projector, or other display device known in the art. Display device 120 may be configured to receive data from image processing device 102, and to display input images, intermediate images, and super-resolution output images. For example, the image processing device 102 may concurrently display via display device 120 an input image, a super-resolution output image generated from the input image, and one or more intermediate images generated during the process of generating the super-resolution output image from the input image. Display device 120 may be combined with processor 104, non-transitory memory 106, and/or user input device 130 in a shared enclosure, or may be a peripheral display device and may comprise a monitor, touchscreen, projector, or other display device known in the art, which may enable a user to view images, and/or interact with various data stored in non-transitory memory 106.

It should be understood that image processing system 100 shown in FIG. 1 is for illustration, not for limitation. Another appropriate image processing system may include more, fewer, or different components.

Figure 2:
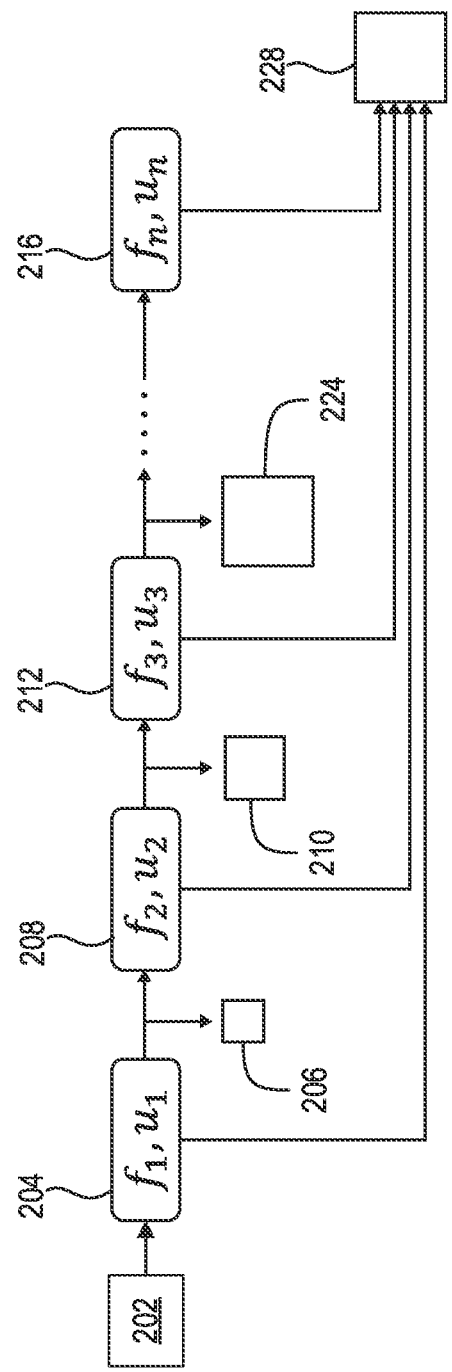
FIG. 2 shows a block diagram illustrating progressive sub-voxel up-sampling of an input image according to an embodiment.

Referring to FIG. 2, a schematic diagram illustrating progressive up-sampling of an input image to a super-resolution output image is shown. The progressive up-sampling of the input image to the super-resolution output image may be performed by an image processing system, such as the image processing system 100 described above. For example, the progressive up-sampling may be performed by an electronic controller (e.g., processor 104) including instructions stored to memory (e.g., memory 106) for performing the routines described herein. The electronic controller includes a deep-learning module configured to adjust images via a deep-learning algorithm (e.g., deep neural network) stored in the memory of the controller. The deep-learning module may be trained separately from the controller and then stored to the memory of the controller, in some examples. In other examples the deep-learning algorithm may be trained by a training module (e.g., training module 112) based on images provided to the training module.

The deep-learning algorithm can be aliased as a super-resolution algorithm, and it constitutes the feature extraction module and up-sampling module. A resolution of the output image may be, for example, twice an expected resolution of input images to be provided to the deep-learning algorithm and to be converted to super-resolution images by the deep-learning algorithm. For training the deep-learning algorithm, the high-resolution image is processed to generate one or more intermediate low-resolution images, and also the ultimate low-resolution input image. The deep-learning algorithm takes in the ultimate low-resolution image as input, and it generates one or more intermediate images, and also the final high-resolution image. The final loss is a summation of loss at each stage, computed using the intermediate images generated earlier, and also the loss of the final high-resolution image.

For example, in order to train the up-sampling module to generate a super-resolution output image from an input image, including generation of a single intermediate image having a resolution that is a multiple of a resolution of the input image, higher than the resolution of the input image, and can be any positive real value and not necessarily an integer value, and where the resolution of the output image is twice the resolution of the input image, there is a high-resolution image as provided as a ground truth image with a scale 2×. The ground truth image may be referred to herein as Image C. The Image C is processed to generate two low-resolution images: one at an intermediate low-resolution (for example, 1.5× scale in this case) that may be referred to herein as Image B, and one at the ultimate low-resolution (e.g., 1× scale), which may be referred to herein as Image A. While training the deep-learning model, the Image A is provided as input, and the model predicts an intermediate image (e.g., 1.5× scale) which may be referred to herein as Image B'. The model also predicts a final output image (e.g., at 2× resolution), which may be referred to herein as Image C'. Loss is computed at each stage, and the final loss is a combination of loss between Image B and Image B', and Image C and Image C'.

The block diagram 200 illustrated by FIG. 2 shows a sequence of generating a super-resolution output image from an input image, where at least one intermediate image is generated from the input image, and the super-resolution output image is generated using the at least one intermediate image. In FIG. 2, the input image, intermediate images, and super-resolution output image are indicated schematically.

The input image 202 is provided to module 204 including the feature learner and sub-voxel up-sampling module. The sub-voxel up-sampling module may be configured based on the problem or imaging modality that is targeted for the up-sampling process. As one example, the sub-voxel up-sampling module is a learnable sub-module in the deep neural network, and may be a part of trainable parameters θ. As another example, the sub-voxel up-sampling module may be medical imaging modality-specific operation, such as zero padding in k-space for magnetic resonance (MR) images. The input image 202 is processed via the module 204 to generate a first intermediate image 206, where a resolution of the first intermediate image 206 is larger than the resolution of the input image 202 (e.g., the resolution of the first intermediate image 206 is equal to the resolution of the input image 202 multiplied by a first non-integer scaling factor greater than 1). The first intermediate image 206 is then provided to module 208, where module 208 includes the feature learner and sub-voxel up-sampling module. For each stage of the up-sampling process (e.g., each portion of the up-sampling process in which an image is provided to a module including the feature learner and sub-voxel up-sampling module), different weights and/or parameters may be learned by the respective module used for the up-sampling. For example, the weights and/or parameters of module 208 may be different than the weights and/or parameters of module 212. The first intermediate image 206 is processed via the module 208 to generate a second intermediate image 210, where a resolution of the second intermediate image 210 is larger than the resolution of the first intermediate image 206 (e.g., the resolution of the second intermediate image 210 is equal to the resolution of the input image 202 multiplied by a second non-integer scaling factor greater than 1 and greater than the first non-integer scaling factor). The second intermediate image 210 is then provided to module 212, where module 212 includes the feature learner and sub-voxel up-sampling module. The second intermediate image 210 is processed via the module 212 to generate a third intermediate image 224, where a resolution of the third intermediate image 224 is larger than the resolution of the second intermediate image 210 (e.g., the resolution of the third intermediate image 224 is equal to the resolution of the input image 202 multiplied by a third non-integer scaling factor greater than 1 and greater than each of the first non-integer scaling factor and the second non-integer scaling factor).

Additional intermediate images may be generated based on a selection made by the user (e.g., input by the user via a user interface device, such as the user input device 130 described above with reference to FIG. 1), where the selection made by the user may result in a different trained neural network being used to generate a super-resolution output image from an input image. For example, a neural network model configured to up-sample an input image to a super-resolution output image may be trained for n stages to generate n outputs: (n−1) intermediate and 1 final output. During conditions in which the user selects up-sampling using n intermediate images, the input image may be processed by the neural network trained for n stages. A neural network trained for 4 stages can generate 4 outputs (3 intermediate+1 output). However, such network may not be used if the user selects to see k images where k>4 (e.g., if k is 6). Prior to initiating the generation of the super-resolution output image from the input image, the user may enter a selection of a number of intermediate images to be generated (e.g., first intermediate image 206, second intermediate image 210, third intermediate image 224, etc.) during the process of generating the super-resolution output image from the input image. The final intermediate image generated during the process of the progressive up-sampling is provided to module 216, where module 216 includes the feature learner and sub-voxel up-sampling module trained for stages (number of intermediate images) greater than or equal to the user-selected number. The module 216 generates super-resolution output image 228, with the super-resolution output image 228 being based on the input image and each of the intermediate images. In particular, the first intermediate image 206 is generated from the input image, the second intermediate image 210 is generated from the first intermediate image 206, and so forth, until the super-resolution output image 228 is generated from the final intermediate image.

In the example shown, the progressive sub-voxel up-sampling of the input image to generate the super-resolution output image may be represented by the equation $I_{sr}=f_n(f_{n-1}(f_{n-2}(\ldots(f_1(I_{lr}, r_1; \theta_1)), r_{n-2}; \theta_{n-2}) r_{n-1}; \theta_{n-1}), s;\theta_n)$, where s is the final expected resolution of the super-resolution output image $I_{sr}$, $\{r_i\}_{i=1}^{n-1}$ are intermediate up-sampling points, and $\{\theta_i\}_{i=1}^{n-1}$ are parameters of the deep-learning module (e.g., deep neural network).

As described above, loss may be calculated to provide training of the deep-learning module. For example, lower resolution intermediate images may be generated from a high-resolution image provided to the training module. The loss for each stage is calculated between the corresponding predicted intermediate image and the processed intermediate ground truth image. The deep-learning module may then be updated based on the calculated loss. The loss may be calculated for a plurality of intermediate images generated, where a resolution of each intermediate image is a different non-integer multiple of an expected resolution of input images to be provided to the deep-learning module for up-sampling to super-resolution output images, and the deep-learning module may be updated following generation of each intermediate image based on the loss between the corresponding predicted intermediate image and the processed intermediate ground truth image.

Figure 3:
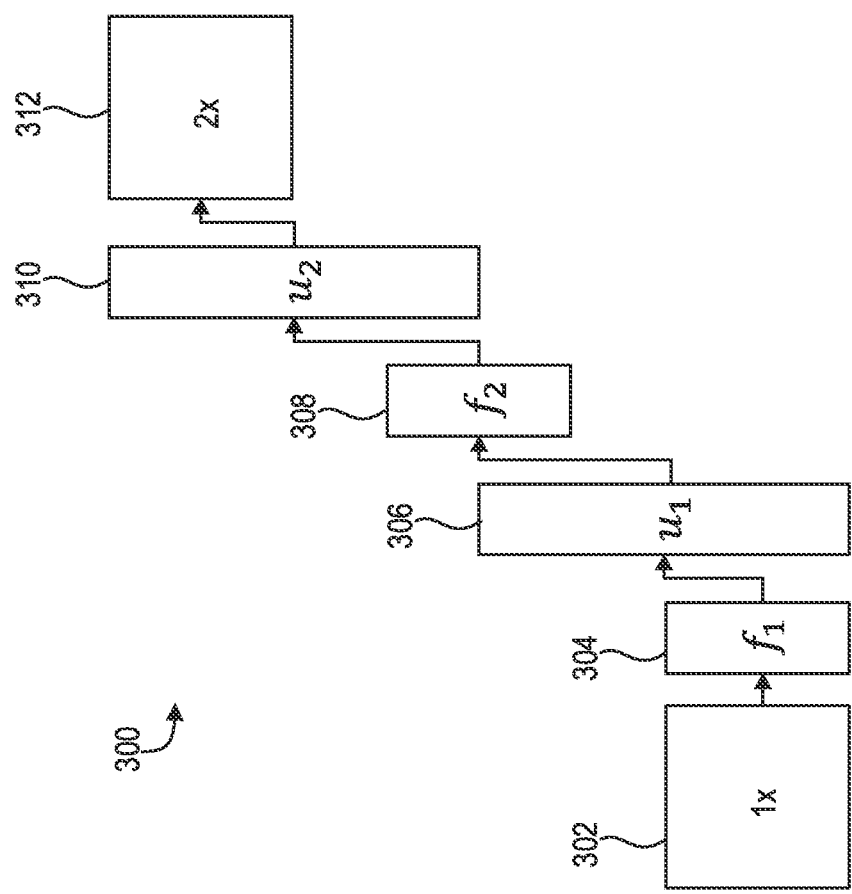
FIG. 3 shows a block diagram illustrating a sequence of progressive up-sampling of an input image to a super-resolution output image using one intermediate image.

As one example of progressive sub-voxel up-sampling of an input image, FIG. 3 shows a block diagram 300 illustrating a sequence of progressive sub-voxel up-sampling of an input image 302 to a super-resolution output image 312 (with the input image 302 and the super-resolution output image 312 indicated schematically). In the example shown, a scale of the input image 302 is 1×, and a scale of the super-resolution output image 312 is 2× (e.g., the super-resolution output image 312 includes twice as many voxels as the input image 302). The super-resolution output image 312 is generated from the input image 302 by computing a single intermediate image as described below. The progressive sub-voxel up-sampling may be performed by an image processing system such as the image processing system 100 described above with reference to FIG. 1.

The input image 302 is provided to feature learner 304 and sub-voxel up-sampling module 306 (e.g., loaded from memory and input to the feature learner 304 and sub-voxel up-sampling module 306). The feature learner 304 and sub-voxel up-sampling module 306 may each be included within a deep neural network, as described above. An output of the sub-voxel up-sampling module 306 is an intermediate image having a higher resolution than the input image 302. In particular, the resolution of the intermediate image is equal to the resolution of the input image 302 multiplied by a non-integer scaling factor (e.g., 1.5). The intermediate image is provided as an input to the feature learner 308 and the sub-voxel up-sampling module 310 (where feature learner 308 and sub-voxel up-sampling module 310 are each included by the deep neural network), and an output of the sub-voxel up-sampling module 310 is the super-resolution output image 312 (e.g., the super-resolution output image 312 is generated based on each of the input image 302 and the intermediate image, with the intermediate image generated based on the input image 302). In the example shown, the resolution of the super-resolution output image 312 is equal to twice the resolution of the input image 302 (e.g., the scale of the super-resolution output image 312 is 2×, and the scale of the input image is 1×).

Figure 4:
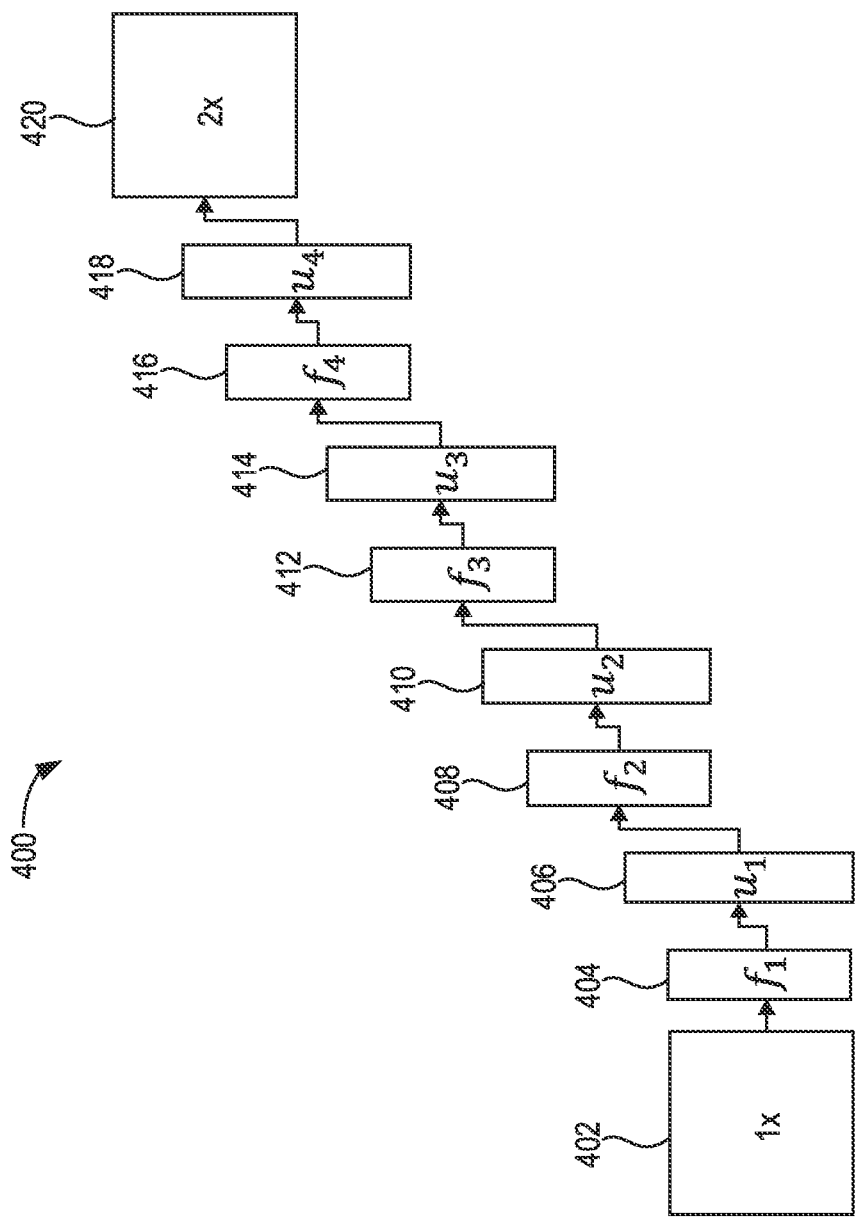
FIG. 4 shows a block diagram illustrating a sequence of progressive up-sampling of an input image to a super-resolution output image using one three intermediate images.

As another example of progressive sub-voxel up-sampling of an input image, FIG. 4 shows a block diagram 400 illustrating a sequence of progressive sub-voxel up-sampling of an input image 402 to a super-resolution output image 420 (with the input image 402 and the super-resolution output image 420 indicated schematically). In the example shown, a scale of the input image 402 is 1×, and a scale of the super-resolution output image 420 is 2× (e.g., the super-resolution output image 420 includes twice as many voxels as the input image 402). The super-resolution output image 420 is generated from the input image 402 by computing more than one intermediate image as described below. The progressive sub-voxel up-sampling may be performed by an image processing system such as the image processing system 100 described above with reference to FIG. 1.

In the example shown by FIG. 4, three intermediate images are generated during the process of generating the super-resolution output image 420 from the input image 402. Each of the feature learners and sub-voxel up-sampling modules in the example shown by FIG. 4 may be included by a deep neural network. The input image 402 is provided to feature learner 404 and sub-voxel up-sampling module 406 (e.g., loaded from memory and input to the feature learner 404 and sub-voxel up-sampling module 406). An output of the sub-voxel up-sampling module 406 is a first intermediate image having a higher resolution than the input image 402 (e.g., similar to first intermediate image 206 described above with reference to FIG. 2). In particular, the resolution of the first intermediate image is equal to the resolution of the input image 402 multiplied by a first non-integer scaling factor (e.g., 1.25). The first intermediate image is provided as an input to the feature learner 408 and the sub-voxel up-sampling module 410, and an output of the sub-voxel up-sampling module 410 is a second intermediate image having a larger resolution than the first intermediate image. In particular, the resolution of the second intermediate image is equal to the resolution of the input image 402 multiplied by a second non-integer scaling factor larger than the first non-integer scaling factor (e.g., 1.5). The second intermediate image is provided as an input to the feature learner 412 and the sub-voxel up-sampling module 414, and an output of the sub-voxel up-sampling module 414 is a third intermediate image having a larger resolution than each of the input image 402, the first intermediate image, and the second intermediate image. In particular, the resolution of the third intermediate image is equal to the resolution of the input image 402 multiplied by a third non-integer scaling factor larger than each of the first non-integer scaling factor and the second non-integer scaling factor (e.g., 1.75).

In the example described above, the first intermediate image has a scaling factor of 1.25 relative to the input image, the second intermediate image has a scaling factor of 1.5 relative to the input image, and the third intermediate image has scaling factor of 1.75 relative to the input image. Each scaling factor in the example described above is different from each other sequentially-adjacent scaling factor by a difference of 0.25 (e.g., the difference between the scaling factor of the first intermediate image and the input image is 0.25, the difference between the scaling factor of the second intermediate image and the first intermediate image is 0.25, etc.). However, the scaling factors may be distributed non-uniformly in some examples. As one example, the scaling factor of the input image may be 1.0, the scaling factor of the first intermediate image may be 1.4, the scaling factor of the second intermediate image may be 1.6, the scaling factor of the third intermediate image may be 1.8, and the scaling factor of the super-resolution output image may be 2.0. In this example, the difference between the scaling factor of the first intermediate image and the scaling factor of the input image is 0.4, but the difference between the scaling factor of the second intermediate image and the first intermediate image is 0.2. Other examples are possible.

The third intermediate image is provided as an input to the feature learner 416 and the sub-voxel up-sampling module 418, and an output of the sub-voxel up-sampling module 418 is the super-resolution output image 420 (e.g., the super-resolution output image 420 is generated based on each of the input image 402, the first intermediate image generated from the input image 402, the second intermediate image generated from the first intermediate image, and the third intermediate image generated from the second intermediate image). In the example shown, the resolution of the super-resolution output image 420 is equal to twice the resolution of the input image 402 (e.g., the scale of the super-resolution output image 420 is 2×, and the scale of the input image 402 is 1×), similar to the example described above with reference to FIG. 3. However, while in the example described above with reference to FIG. 3 a single intermediate image was generated to progressively up-sample the input image to the super-resolution output image, in the example described above with reference to FIG. 4, three intermediate images are generated to progressively up-sample the input image to the super-resolution output image. By increasing the number of intermediate images, a user of the image processing system (e.g., an operator, such as a technician) may evaluate each of the intermediate images alongside the input image and the super-resolution output image, which may increase an ease of identification of features (e.g., anatomical features) shown by the images and increase a confidence of patient diagnosis (e.g., a patient having anatomical features shown by the images).

Figure 5:
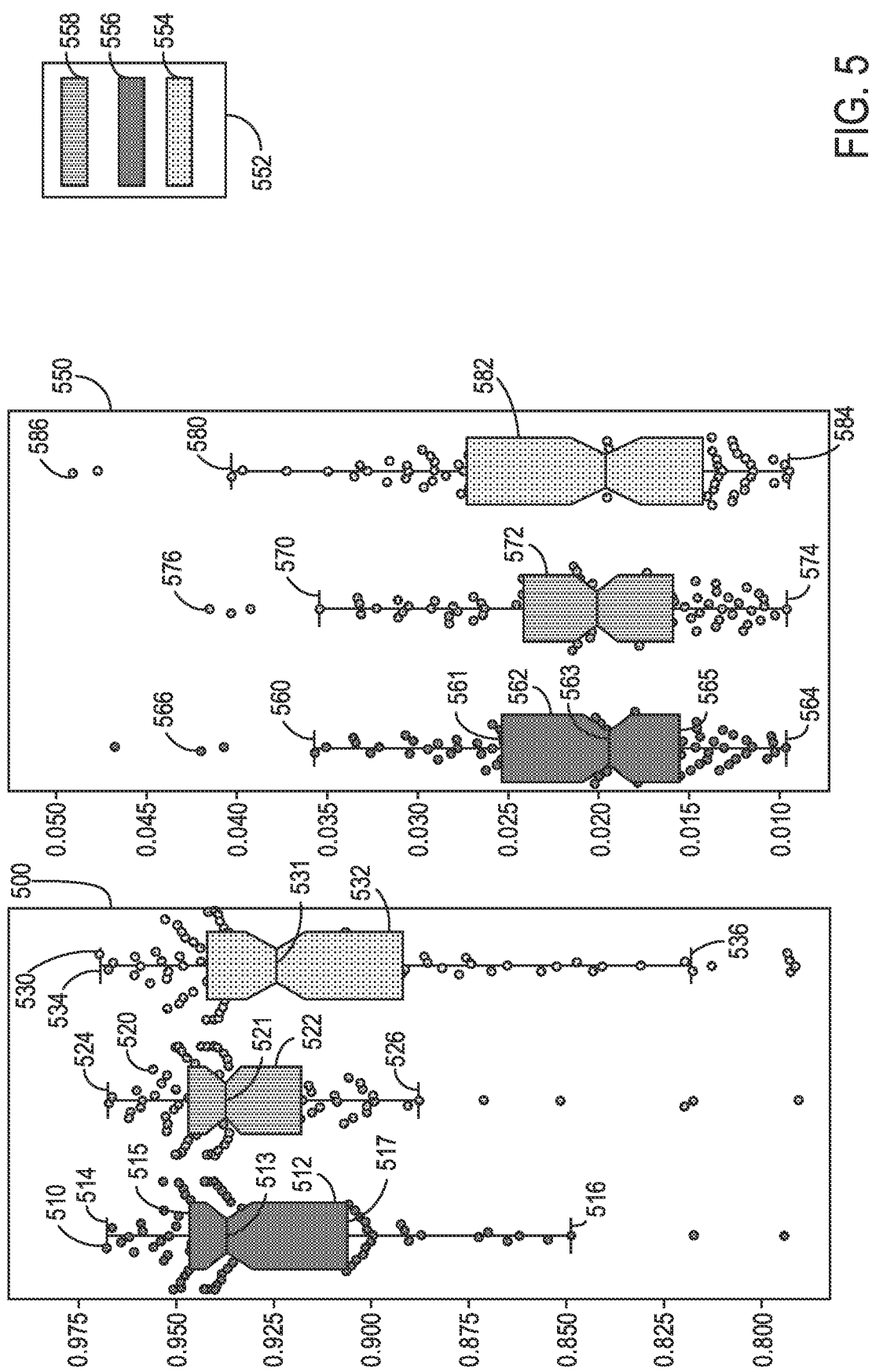
FIG. 5 shows graphs illustrating experimental results of progressive sub-voxel up-sampling of input images to super-resolution output images.

Referring to FIG. 5, various graphs are shown illustrating experimental results of progressive sub-voxel up-sampling according to the methods described herein. In particular, a first graph 500 is shown illustrating experimentally-observed values of a Structural Similarity Index (SSIM) for up-sampling an input image to a super-resolution output image, and a second graph 550 illustrates experimentally-observed values of Laplacian loss for up-sampling an input image to a super-resolution output image, where in each case the metrics are computed on a test set, separate from the training. Legend 552 shows first shading 554, second shading 556, and third shading 558. In the first graph 500 and second graph 550, the first shading 554 indicates experimental results observed by generating a super-resolution output image from an input image with no intermediate images generated, the second shading 556 indicates experimental results observed by generating a super-resolution output image from an input image with a single intermediate image generated (e.g., similar to the example described above with reference to FIG. 3), and the third shading 558 indicates experimental results observed by generating a super-resolution output image from an input image with three intermediate images generated (e.g., similar to the example described above with reference to FIG. 4).

The first graph 500 includes a plurality of experimental data points 530 shaded with the first shading 554, a plurality of experimental data points 510 shaded with the second shading 556, and a plurality of experimental data points 520 shaded with the third shading 558. Each of the data points 530 represents the SSIM of a super-resolution output image generated from an input image with no intermediate images generated from the input image (e.g., with the super-resolution output image generated directly from the input image, with the super-resolution output image not based on any intermediate images generated from the input image), where in each case the metrics are computed on a test set, separate from the training. Each of the data points 510 represents the SSIM of a super-resolution output image generated from an input image with a single intermediate image generated with a resolution greater than a resolution of the input image and less than a resolution of the super-resolution output image (e.g., similar to the example described above with reference to FIG. 3, where the intermediate image is generated from the input image and the super-resolution output image is generated from the intermediate image), where in each case the metrics are computed on a test set, separate from the training. Each of the data points 520 represents the SSIM of a super-resolution output image generated from an input image with three intermediate images generated with a resolution greater than a resolution of the input image and less than a resolution of the super-resolution output image (e.g., similar to the example described above with reference to FIG. 4, where a first intermediate image is generated from the input image, a second intermediate image is generated from the first intermediate image, a third intermediate image is generated from the second intermediate image, and the super-resolution output image is generated from the third intermediate image), where in each case the metrics are computed on a test set, separate from the training.

The first graph 500 includes plot 512 (which may be referred to herein as a box plot) illustrating an average of the data points 510, plot 522 illustrating an average of the data points 520, and plot 532 illustrating an average of the data points 530. In the plot 512, each of the horizontal lines of the plot 512 represents a quantile of the data. In particular, lower horizontal line 517 shows the 25th percentile, middle horizontal line 513 shows the median, and upper horizontal line 515 shows the 75th percentile. The size of the box plot represents the variability in the data points, e.g., smaller sizes represent smaller variabilities. The uppermost horizontal line 514 represents Q1−1.5×IQR and the lowermost horizontal line 516 represents Q3+1.5×IQR, where IQR is inter-quartile range. Each of the other plots included by the first graph 500 include horizontal lines indicating the parameters similar to those described above with reference to plot 512. For example, middle horizontal line 521 showing the median of the data points 520, etc. Plot 532 includes middle horizontal line 531 showing the median of the data points 530, etc.

As shown by the first graph 500, the average SSIM illustrated by the plot 522 is higher than the average SSIM illustrated by the plot 512, and the average SSIM illustrated by the plot 512 is higher than the average SSIM illustrated by the plot 532. The average SSIM for the super-resolution output images generated using three intermediate images, as indicated by plot 522, is greater than the average SSIM for super-resolution output images generated using fewer intermediate images. In the example shown by FIG. 5, the input images are at a scale of 1× and the super-resolution output images are at a scale of 2×. The scale of the three intermediate images generated for each super-resolution output image indicated by the data points 520 is a multiple of the scale of the input image, higher than the scale of the input image, and can be any positive real value and not necessarily an integer value, upon which each super-resolution output image indicated by the data points 520 is based. In particular, the scale of a first intermediate image of the three intermediate images is 1.25×, a scale of a second intermediate image of the three intermediate images is 1.5×, and a scale of a third intermediate image of the three intermediate images is 1.75×. The additional intermediate images generated along with each super-resolution output image indicated by the data points 520 results in increased clarity (e.g., increased contrast of features) of the super-resolution output images relative to super-resolution output images generated with fewer intermediate images or no intermediate images.

The second graph 550 includes a plurality of experimental data points 586 shaded with the first shading 554, a plurality of experimental data points 566 shaded with the second shading 556, and a plurality of experimental data points 576 shaded with the third shading 558. Each of the data points 586 represents the Laplacian loss of a super-resolution output image generated from an input image with no intermediate images generated from the input image (e.g., with the super-resolution output image generated directly from the input image, with the super-resolution output image not based on any intermediate images generated from the input image), where in each case the metrics are computed on a test set, separate from the training. Each of the data points 566 represents the Laplacian loss of a super-resolution output image generated from an input image, with a single intermediate image generated with a resolution greater than a resolution of the input image and less than a resolution of the super-resolution output image (e.g., similar to the example described above with reference to FIG. 3, where the intermediate image is generated from the input image and the super-resolution output image is generated from the intermediate image), where in each case the metrics are computed on a test set, separate from the training. Each of the data points 576 represents the Laplacian loss of a super-resolution output image generated from an input image, with three intermediate images generated with a resolution greater than a resolution of the input image and less than a resolution of the super-resolution output image (e.g., similar to the example described above with reference to FIG. 4, where a first intermediate image is generated from the input image, a second intermediate image is generated from the first intermediate image, a third intermediate image is generated from the second intermediate image, and the super-resolution output image is generated from the third intermediate image), where in each case the metrics are computed on a test set, separate from the training.

The second graph 550 includes plot 582 (e.g., box plot) illustrating an average of the data points 586, plot 562 illustrating an average of the data points 566, and plot 572 illustrating an average of the data points 576. In the plot 582, each of the horizontal lines of the plot 582 represents a quantile of the data. In particular, lower horizontal line 565 shows the 25th percentile, middle horizontal line 563 shows the median, and upper horizontal line 561 shows the 75th percentile. The size of the box plot represents the variability in the data points, e.g., smaller sizes represent smaller variabilities. The uppermost horizontal line 560 represents Q1−1.5×IQR and the lowermost horizontal line 564 represents Q3+1.5×IQR, where IQR is inter-quartile range. Each of the other plots included by the second graph 550 include horizontal lines indicating the parameters similar to those described above with reference to plot 582. For example, plot 572 includes uppermost horizontal line 570 representing Q1−1.5×IQR and lowermost horizontal line 574 representing Q3+1.5×IQR, where IQR is inter-quartile range. Plot 582 includes uppermost horizontal line 580 representing Q1−1.5×IQR and lowermost horizontal line 584 representing Q3+1.5×IQR, where IQR is inter-quartile range.

As shown by the second graph 550, the average Laplacian loss illustrated by the plot 572 is lower than the average Laplacian loss illustrated by the plot 562, and the average Laplacian loss illustrated by the plot 562 is lower than the average Laplacian loss illustrated by the plot 582. The average Laplacian loss for the super-resolution output images generated using three intermediate images, as indicated by plot 572, is lower than the average Laplacian loss for super-resolution output images generated using fewer intermediate images. In the example shown by FIG. 5, the input images are at a scale of 1× and the super-resolution output images are at a scale of 2×. The scale of the three intermediate images generated for each super-resolution output image indicated by the data points 576 is a multiple of the scale of the input image (and is higher than the scale of the input image and can be any positive real value and not necessarily an integer value) upon which each super-resolution output image indicated by the data points 576 is based. In particular, the scale of a first intermediate image of the three intermediate images is 1.25×, a scale of a second intermediate image of the three intermediate images is 1.5×, and a scale of a third intermediate image of the three intermediate images is 1.75×. The additional intermediate images generated along with each super-resolution output image indicated by the data points 576 results in increased clarity (e.g., increased contrast of features) of the super-resolution output images relative to super-resolution output images generated with fewer intermediate images or no intermediate images.

Referring to FIG. 6, a block diagram 600 is shown schematically illustrating a modality-specific sub-voxel up-sampling module 601. As one example, the sub-voxel up-sampling module 601 may be particular to the MR imaging modality (e.g., the sub-voxel up-sampling module may be configured to process MR images with increased clarity relative to modules that are not particular to the MR imaging modality). The sub-voxel up-sampling module 601 may receive an input image 602 and may generate an output image 610 based on the input image. As one example, the input image 602 may be similar to, or the same as, the input image 202 described above with reference to FIG. 2, and the output image may be an intermediate image generated from the input image 202 (e.g., where a super-resolution output image is generated from the intermediate image). As another example, the input image may be an intermediate image generated during the process of up-sampling a lower-resolution input image to a super-resolution output image, and the output image 610 may be the super-resolution output image.

The sub-voxel up-sampling module 601 may be provided the input image 602, and the sub-voxel up-sampling module 601 applies a Fourier transform 604 to the image data (e.g., voxel data) included by the input image 602. The sub-voxel up-sampling module 601 then applies a zero-padding to the K-space of the input image 602 at block 606, and an inverse Fourier transform 608 is then applied to generate the output image 610. As one example, the FFT may transform the image data to k-space, where the k-space is raw image data stored in a matrix and not mapped to image space. The matrix may be expanded, and points of the matrix that are not filled with image data may be filled with zero to perform the zero-padding. The matrix data may then be transformed back to image space. For the MR modality, the up-sampling operation may be performed in the frequency domain, e.g., the k-space of the input image. For example, to up-sample an input image with a width of 100 voxels and a height of 100 voxels to a 1.5× up-sampled version with a width of 150 voxels and a height of 150 voxels, the FFT may be applied to the input image to acquire the k-space of the input image, the k-space may be padded with 25 points in all four directions (e.g., 25 points in each width direction and 25 points in each height direction), and the inverse FFT may be applied to bring the data back to the image domain. As a result, the image is up-sampled to the desired 1.5× scale.

Referring to FIG. 7, another block diagram 700 is shown illustrating a sequence of progressive sub-voxel up-sampling of an input image 702 to a super-resolution output image 712 (with the input image 702 and the super-resolution output image 712 indicated schematically). In the example shown, a scale of the input image 702 is 1×, and a scale of the super-resolution output image 712 is 2× (e.g., the super-resolution output image 712 includes twice as many voxels as the input image 702). The super-resolution output image 712 is generated from the input image 702 by computing a single intermediate image. The progressive sub-voxel up-sampling may be performed by an image processing system such as the image processing system 100 described above with reference to FIG. 1.

In the example shown by FIG. 7, the input image 702 is provided to a sub-voxel up-sampling module 704 and feature learner 706 to generate an intermediate image having a resolution higher than a resolution of the input image 702.

The intermediate image is then provided to sub-voxel up-sampling module 708 and feature learner 710 to generate the super-resolution output image 712. In the example shown by FIG. 7, the sub-voxel up-sampling module 704 and the sub-voxel up-sampling module 708 are each modality-specific sub-voxel up-sampling modules. For example, the sub-voxel up-sampling module 704 and the sub-voxel up-sampling module 708 may each be similar to, or the same as, the sub-voxel up-sampling module 601 described above with reference to FIG. 6.

Figure 8:
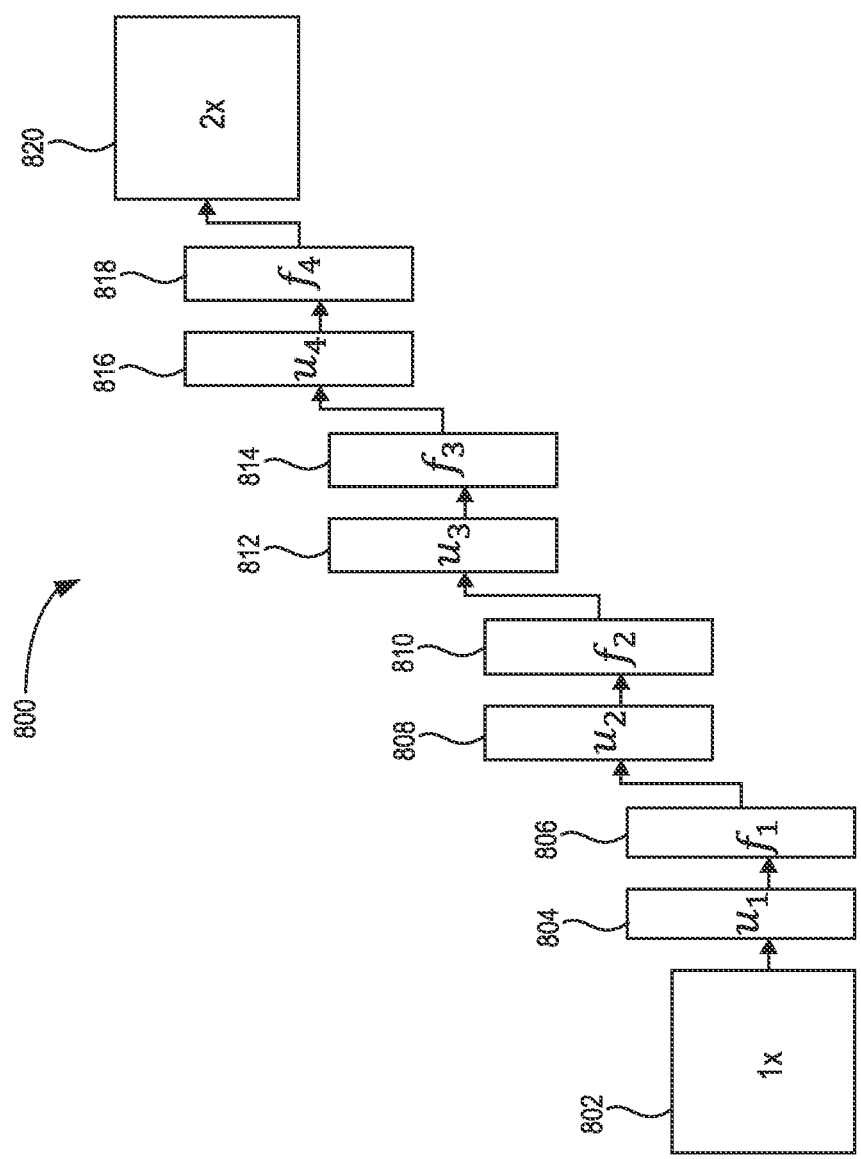
FIG. 8 shows a block diagram illustrating a sequence of modality-specific progressive up-sampling of an input image to a super-resolution output image using three intermediate images.

Referring to FIG. 8, another block diagram 800 is shown illustrating a sequence of progressive sub-voxel up-sampling of an input image 802 to a super-resolution output image 820 (with the input image 802 and the super-resolution output image 820 indicated schematically). In the example shown, a scale of the input image 802 is 1×, and a scale of the super-resolution output image 820 is 2× (e.g., the super-resolution output image 820 includes twice as many voxels as the input image 802). The super-resolution output image 820 is generated from the input image 802 by computing a plurality of intermediate images as described below. The progressive sub-voxel up-sampling may be performed by an image processing system such as the image processing system 100 described above with reference to FIG. 1.

In the example shown by FIG. 8, the input image 802 is provided to a sub-voxel up-sampling module 804 and feature learner 806 to generate a first intermediate image having a resolution higher than a resolution of the input image 802 (e.g., a scale of 1.25× versus the 1× scale of the input image 802). The first intermediate image is then provided to sub-voxel up-sampling module 808 and feature learner 810 to generate a second intermediate image having a resolution higher than the resolution of the first intermediate image (e.g., a scale of 1.5× versus the 1.25× scale of the first intermediate image). The second intermediate image is then provided to sub-voxel up-sampling module 812 and feature learner 814 to generate a third intermediate image having a resolution higher than the resolution of the second intermediate image (e.g., a scale of 1.75× versus the 1.5× scale of the second intermediate image). The third intermediate image is then provided to sub-voxel up-sampling module 816 and feature learner 818 to generate the super-resolution output image 820 having a higher resolution than the third intermediate image (e.g., a scale of 2× versus the 1.75× scale of the third intermediate image). In the example shown by FIG. 8, the sub-voxel up-sampling module 804, the sub-voxel up-sampling module 808, the sub-voxel up-sampling module 812, and the sub-voxel up-sampling module 816 are each modality-specific sub-voxel up-sampling modules. For example, the sub-voxel up-sampling module 804, the sub-voxel up-sampling module 808, the sub-voxel up-sampling module 812, and the sub-voxel up-sampling module 816 may each be similar to, or the same as, the sub-voxel up-sampling module 601 described above with reference to FIG. 6.

Figure 9:
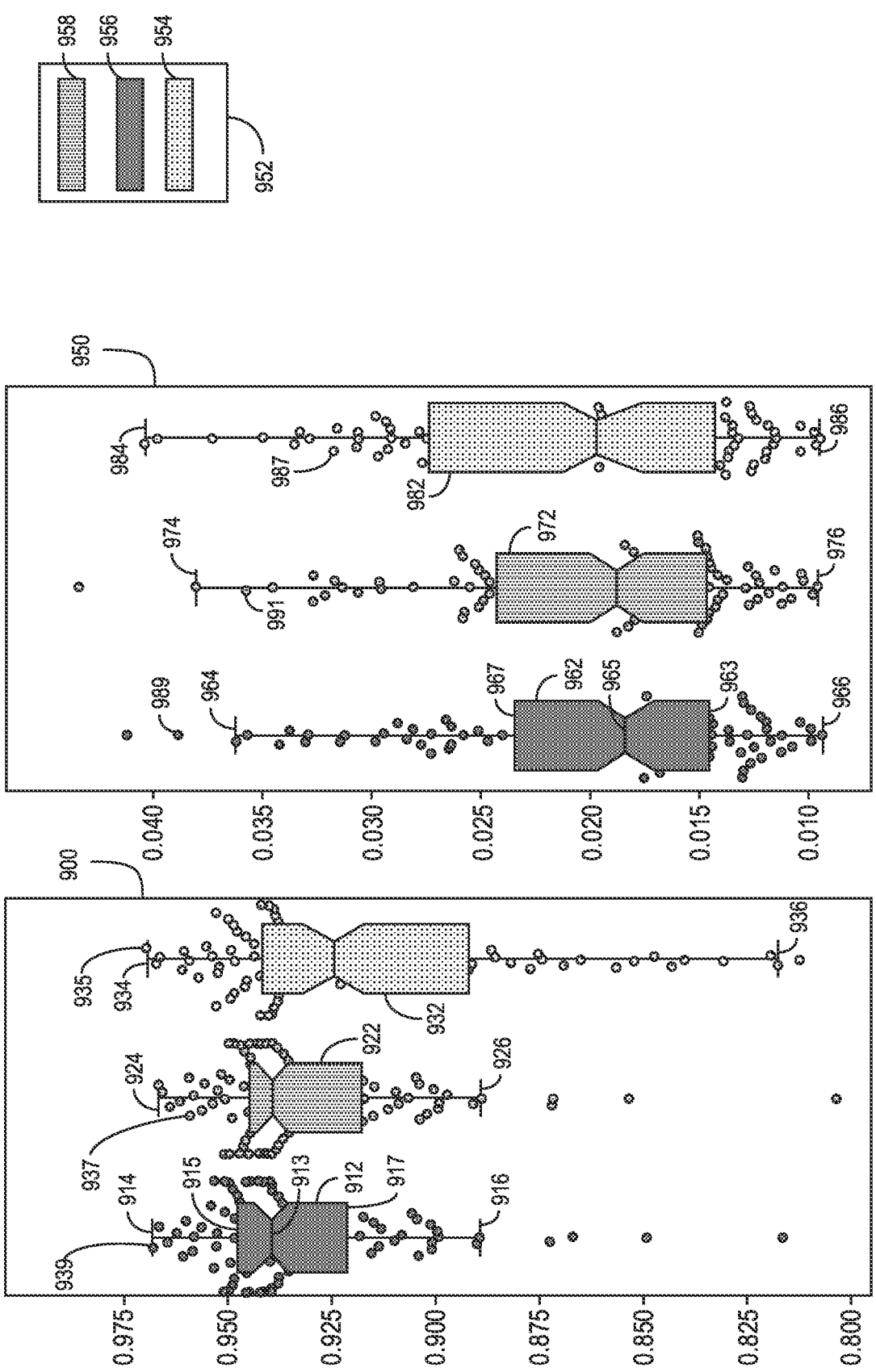
FIG. 9 shows graphs illustrating experimental results of modality-specific progressive sub-voxel up-sampling of input images to super-resolution output images.

Referring to FIG. 9, graphs are shown illustrating experimental results of progressive sub-voxel up-sampling using modality-specific sub-voxel up-sampling modules, according to the methods described herein. In particular, a first graph 900 is shown illustrating experimentally-observed values of a Structural Similarity Index (SSIM) for up-sampling an input image to a super-resolution output image using modality-specific sub-voxel up-sampling modules, and a second graph 950 illustrates experimentally-observed values of Laplacian loss for up-sampling an input image to a super-resolution output image using modality-specific sub-voxel up-sampling modules, where in each case the metrics are computed on a test set, separate from the training.

The configuration of the modality-specific sub-voxel up-sampling modules is the same as the configuration of the sub-voxel up-sampling module 601 shown by FIG. 6 and described above. Legend 952 shows first shading 954, second shading 956, and third shading 958. In the first graph 900 and second graph 950, the first shading 954 indicates experimental results observed by generating a super-resolution output image from an input image with no intermediate images generated where in each case the metrics are computed on a test set separate from the training, the second shading 956 indicates experimental results observed by generating a super-resolution output image from an input image with a single intermediate image generated (e.g., similar to the example described above with reference to FIG. 7) where in each case the metrics are computed on a test set separate from the training, and the third shading 958 indicates experimental results observed by generating a super-resolution output image from an input image with three intermediate images generated (e.g., similar to the example described above with reference to FIG. 8) where in each case the metrics are computed on a test set separate from the training.

The first graph 900 includes a plurality of experimental data points 935 shaded with the first shading 954, a plurality of experimental data points 939 shaded with the second shading 956, and a plurality of experimental data points 937 shaded with the third shading 958. Each of the data points 935 represents the SSIM of a super-resolution output image generated from an input image with no intermediate images generated from the input image (e.g., with the super-resolution output image generated directly from the input image, with the super-resolution output image not based on any intermediate images generated from the input image), where in each case the metrics are computed on a test set separate from the training. Each of the data points 939 represents the SSIM of a super-resolution output image generated from an input image with a single intermediate image generated with a resolution greater than a resolution of the input image and less than a resolution of the super-resolution output image (e.g., similar to the example described above with reference to FIG. 7, where the intermediate image is generated from the input image and the super-resolution output image is generated from the intermediate image), where in each case the metrics are computed on a test set separate from the training. Each of the data points 937 represents the SSIM of a super-resolution output image generated from an input image with three intermediate images generated with a resolution greater than a resolution of the input image and less than a resolution of the super-resolution output image (e.g., similar to the example described above with reference to FIG. 8, where a first intermediate image is generated from the input image, a second intermediate image is generated from the first intermediate image, a third intermediate image is generated from the second intermediate image, and the super-resolution output image is generated from the third intermediate image), where in each case the metrics are computed on a test set separate from the training.

The first graph 900 includes plot 912 (which may be referred to herein as a box plot) illustrating an average of the data points 939, plot 922 illustrating an average of the data points 937, and plot 932 illustrating an average of the data points 935. In the plot 912, each of the horizontal lines of the plot 912 represents a quantile of the data. In particular, lower horizontal line 917 shows the 25th percentile, middle horizontal line 913 shows the median, and upper horizontal line 915 shows the 75th percentile. The size of the box plot represents the variability in the data points, e.g., smaller sizes represent smaller variabilities. The lowermost horizontal line 916 represents Q1−1.5×IQR and the uppermost horizontal line 914 represents Q3+1.5×IQR, where IQR is inter-quartile range. Each of the other plots included by the first graph 900 include horizontal lines indicating the parameters similar to those described above with reference to plot 912. For example, plot 922 includes uppermost horizontal line 924 representing Q1−1.5×IQR associated with data points 937, lowermost horizontal line 926 representing Q3+1.5×IQR associated with data points 937, etc. Plot 932 includes uppermost horizontal line 934 representing Q1−1.5×IQR associated with data points 935, lowermost horizontal line 936 representing Q3+1.5×IQR associated with data points 935, etc.

The second graph 950 includes a plurality of experimental data points 987 shaded with the first shading 954, a plurality of experimental data points 989 shaded with the second shading 956, and a plurality of experimental data points 991 shaded with the third shading 958. Each of the data points 987 represents the Laplacian loss of a super-resolution output image generated from an input image with no intermediate images generated from the input image (e.g., with the super-resolution output image generated directly from the input image, with the super-resolution output image not based on any intermediate images generated from the input image), where in each case the metrics are computed on a test set, separate from the training. Each of the data points 989 represents the Laplacian loss of a super-resolution output image generated from an input image, with a single intermediate image generated with a resolution greater than a resolution of the input image and less than a resolution of the super-resolution output image (e.g., similar to the example described above with reference to FIG. 7, where the intermediate image is generated from the input image and the super-resolution output image is generated from the intermediate image), where in each case the metrics are computed on a test set, separate from the training. Each of the data points 991 represents the Laplacian loss of a super-resolution output image generated from an input image, with three intermediate images generated with a resolution greater than a resolution of the input image and less than a resolution of the super-resolution output image (e.g., similar to the example described above with reference to FIG. 8, where a first intermediate image is generated from the input image, a second intermediate image is generated from the first intermediate image, a third intermediate image is generated from the second intermediate image, and the super-resolution output image is generated from the third intermediate image), where in each case the metrics are computed on a test set, separate from the training.

The second graph 950 includes plot 962 (e.g., box plot) illustrating an average of the data points 989, plot 972 illustrating an average of the data points 991, and plot 982 illustrating an average of the data points 987. In the plot 962, each of the horizontal lines of the plot 962 represents a quantile of the data. In particular, lower horizontal line 963 shows the 25th percentile, middle horizontal line 965 shows the median, and upper horizontal line 967 shows the 75th percentile. The size of the box plot represents the variability in the data points, e.g., smaller sizes represent smaller variabilities. The lowest horizontal line 966 represents Q3+1.5×IQR, and the uppermost horizontal line 964 represents Q1−1.5×IQR. Each of the other plots included by the second graph 950 include horizontal lines indicating the parameters similar to those described above with reference to plot 962. For example, plot 972 includes uppermost horizontal line 974 representing Q1−1.5×IQR associated with the data points 991, lowermost horizontal line 976 representing Q3+1.5×IQR associated with the data points 991, etc. Plot 982 includes uppermost horizontal line 984 representing Q1−1.5×IQR associated with data points 987, lowermost horizontal line 986 representing Q3+1.5×IQR associated with data points 987, etc. As shown by the graphs described above, each of the processes including generation of at least one intermediate image provides results that are more desirable than a process without generation of intermediate images.

Figure 10:
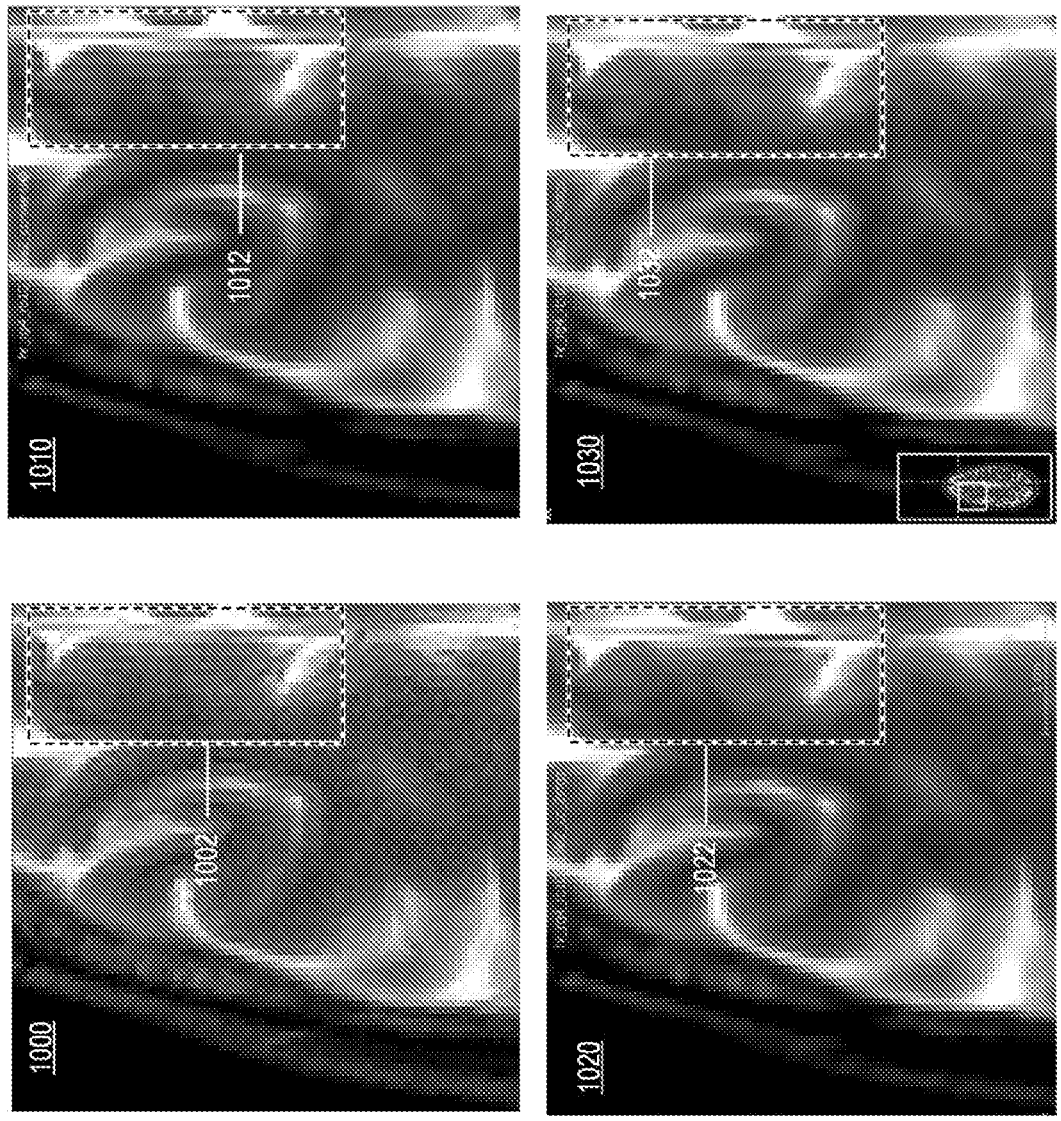
FIG. 10 shows an example input image and three example output images generated from the input image with different parameters.

Referring collectively to FIGS. 10-14, various images are shown illustrating input images and output images generated from the input images. In particular, FIG. 10 shows an input image 1000, a first output image 1010 generated from the input image 1000 without generation of intermediate images, a super-resolution output image 1020 generated from the input image 1000 with one intermediate image (e.g., similar to the examples described above with reference to FIG. 3 and FIG. 7), and a super-resolution output image 1030 generated from the input image 1000 with three intermediate images (e.g., similar to the examples described above with reference to FIG. 4 and FIG. 8). A region of interest is indicated at the input image 1000 via a dashed-line overlay 1002, with the corresponding region of interest indicated at the first output image 1010 by overlay 1012, at the super-resolution output image 1020 by overlay 1022, and at the super-resolution output image 1030 by overlay 1032.

Figure 11:
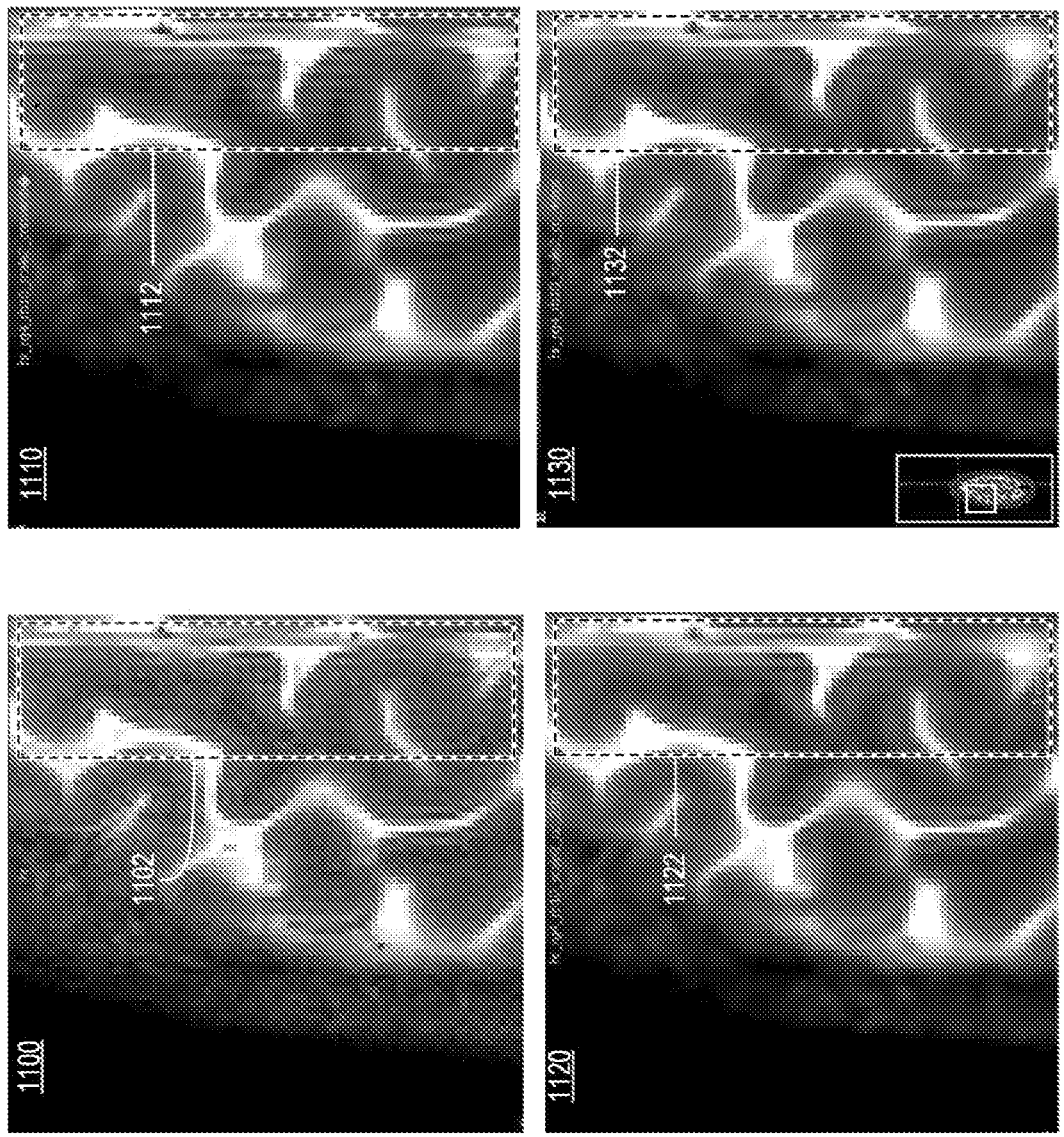
FIG. 11 shows another example input image and three example output images generated from the input image with different parameters.

FIG. 11 shows an input image 1100, a first output image 1110 generated from the input image 1100 without generation of intermediate images, a super-resolution output image 1120 generated from the input image 1100 with one intermediate image (e.g., similar to the examples described above with reference to FIG. 3 and FIG. 7), and a super-resolution output image 1130 generated from the input image 1100 with three intermediate images (e.g., similar to the examples described above with reference to FIG. 4 and FIG. 8). A region of interest is indicated at the input image 1100 via a dashed-line overlay 1102, with the corresponding region of interest indicated at the first output image 1110 by overlay 1112, at the super-resolution output image 1120 by overlay 1122, and at the super-resolution output image 1130 by overlay 1132.

Figure 12:
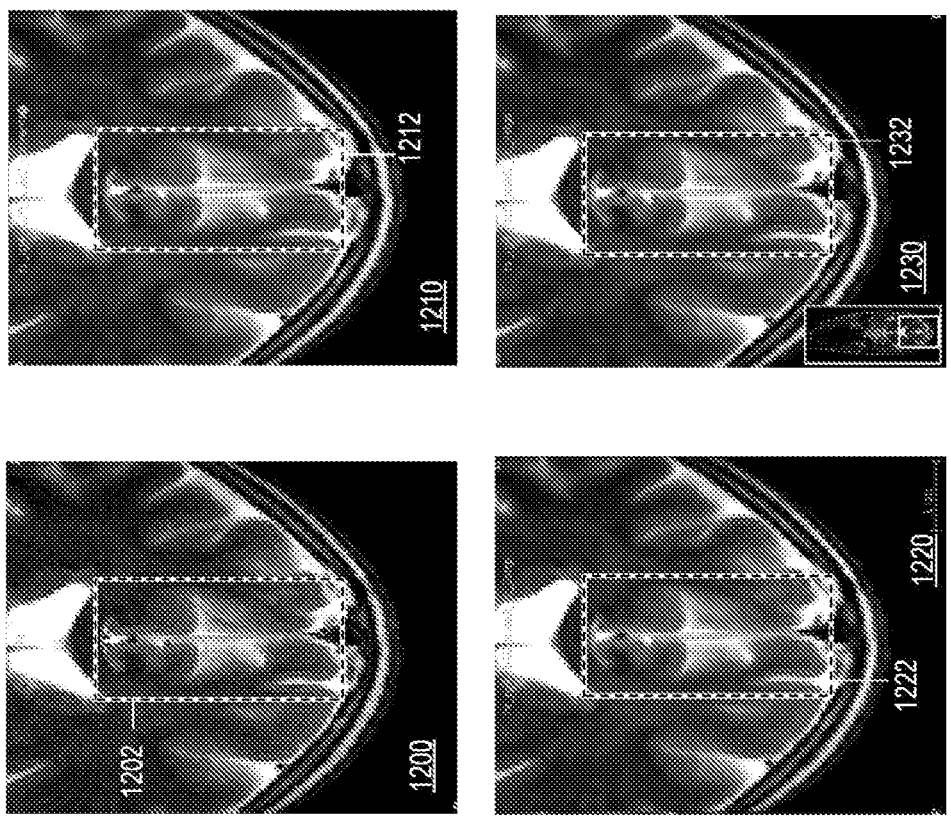
FIG. 12 shows another example input image and three example output images generated from the input image with different parameters.

FIG. 12 shows an input image 1200, a first output image 1210 generated from the input image 1200 without generation of intermediate images, a super-resolution output image 1220 generated from the input image 1200 with one intermediate image (e.g., similar to the examples described above with reference to FIG. 3 and FIG. 7), and a super-resolution output image 1230 generated from the input image 1200 with three intermediate images (e.g., similar to the examples described above with reference to FIG. 4 and FIG. 8). A region of interest is indicated at the input image 1200 via a dashed-line overlay 1202, with the corresponding region of interest indicated at the first output image 1210 by overlay 1212, at the super-resolution output image 1220 by overlay 1222, and at the super-resolution output image 1230 by overlay 1232.

Figure 13:
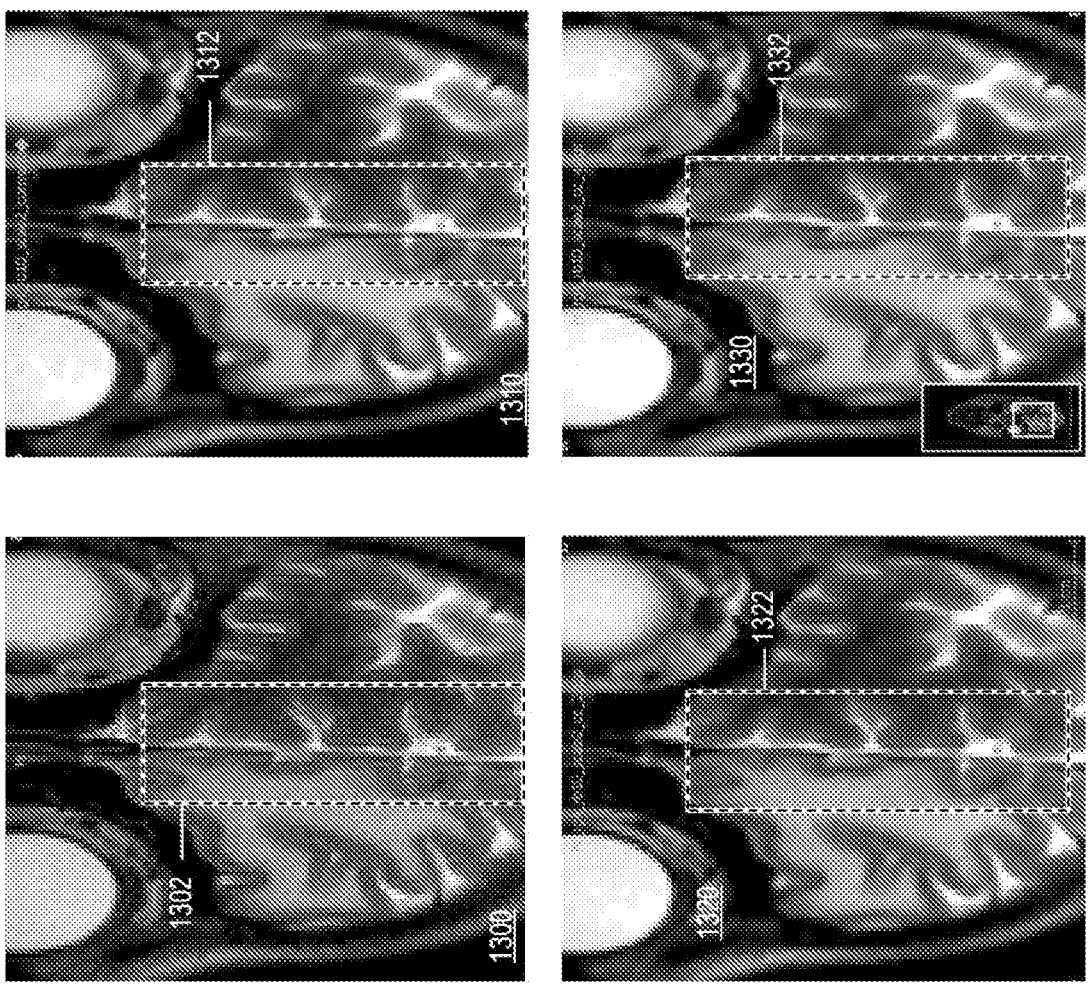
FIG. 13 shows another example input image and three example output images generated from the input image with different parameters.

FIG. 13 shows an input image 1300, a first output image 1310 generated from the input image 1300 without generation of intermediate images, a super-resolution output image 1320 generated from the input image 1300 with one intermediate image (e.g., similar to the examples described above with reference to FIG. 3 and FIG. 7), and a super-resolution output image 1330 generated from the input image 1300 with three intermediate images (e.g., similar to the examples described above with reference to FIG. 4 and FIG. 8). A region of interest is indicated at the input image 1300 via a dashed-line overlay 1302, with the corresponding region of interest indicated at the first output image 1310 by overlay 1312, at the super-resolution output image 1320 by overlay 1322, and at the super-resolution output image 1330 by overlay 1332.

Figure 14:
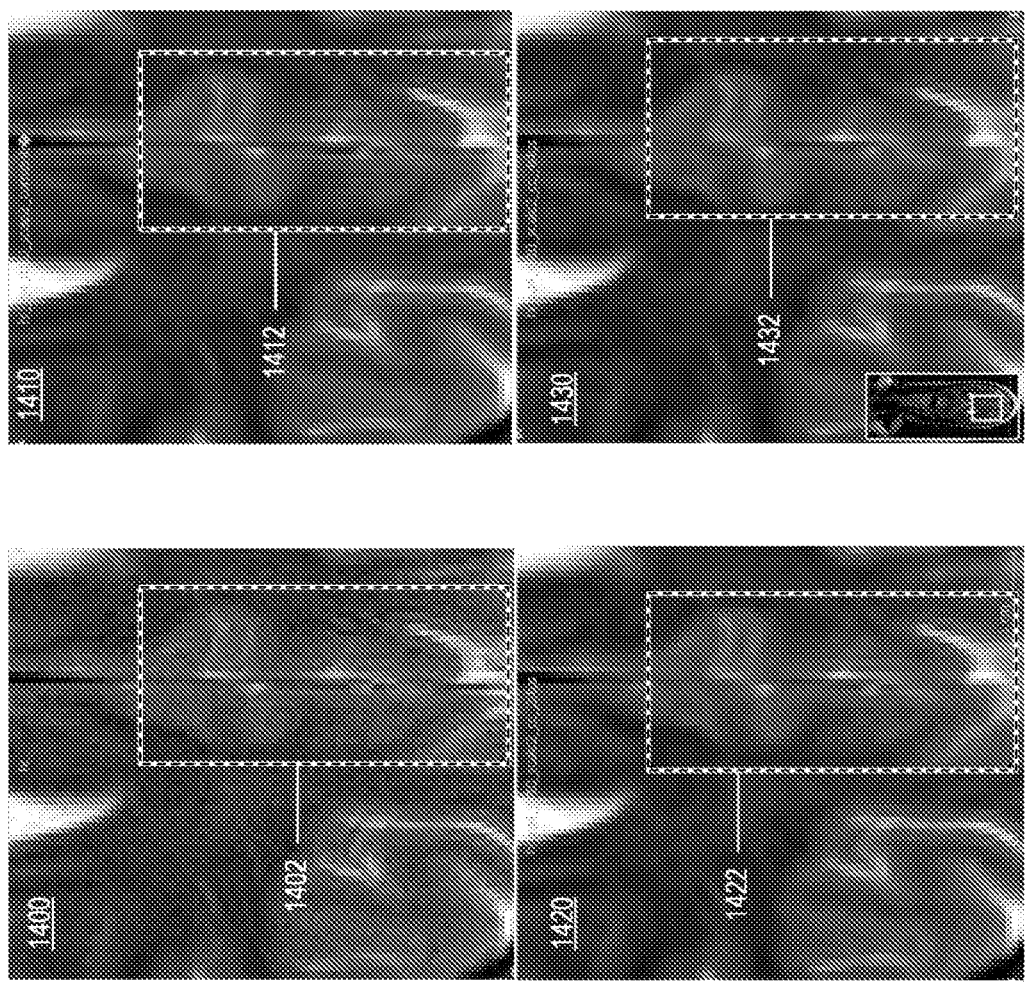
FIG. 14 shows another example input image and three example output images generated from the input image with different parameters.

FIG. 14 shows an input image 1400, a first output image 1410 generated from the input image 1400 without generation of intermediate images, a super-resolution output image 1420 generated from the input image 1400 with one intermediate image (e.g., similar to the examples described above with reference to FIG. 3 and FIG. 7), and a super-resolution output image 1430 generated from the input image 1400 with three intermediate images (e.g., similar to the examples described above with reference to FIG. 4 and FIG. 8). A region of interest is indicated at the input image 1400 via a dashed-line overlay 1402, with the corresponding region of interest indicated at the first output image 1410 by overlay 1412, at the super-resolution output image 1420 by overlay 1422, and at the super-resolution output image 1430 by overlay 1432.

As illustrated by FIGS. 10-14, the super-resolution output images generated via the sub-voxel up-sampling process including generation of three intermediate images have increased clarity relative to the other output images. In particular, the super-resolution output image 1030 shown by FIG. 10 has increased clarity and contrast relative to output image 1020, output image 1010, and input image 1000, the super-resolution output image 1130 shown by FIG. 11 has increased clarity and contrast relative to output image 1120, output image 1110, and input image 1100, the super-resolution output image 1230 shown by FIG. 12 has increased clarity and contrast relative to output image 1220, output image 1210, and input image 1200, the super-resolution output image 1330 shown by FIG. 13 has increased clarity and contrast relative to output image 1320, output image 1310, and input image 1300, and the super-resolution output image 1430 shown by FIG. 14 has increased clarity and contrast relative to output image 1420, output image 1410, and input image 1400.

Figure 15:
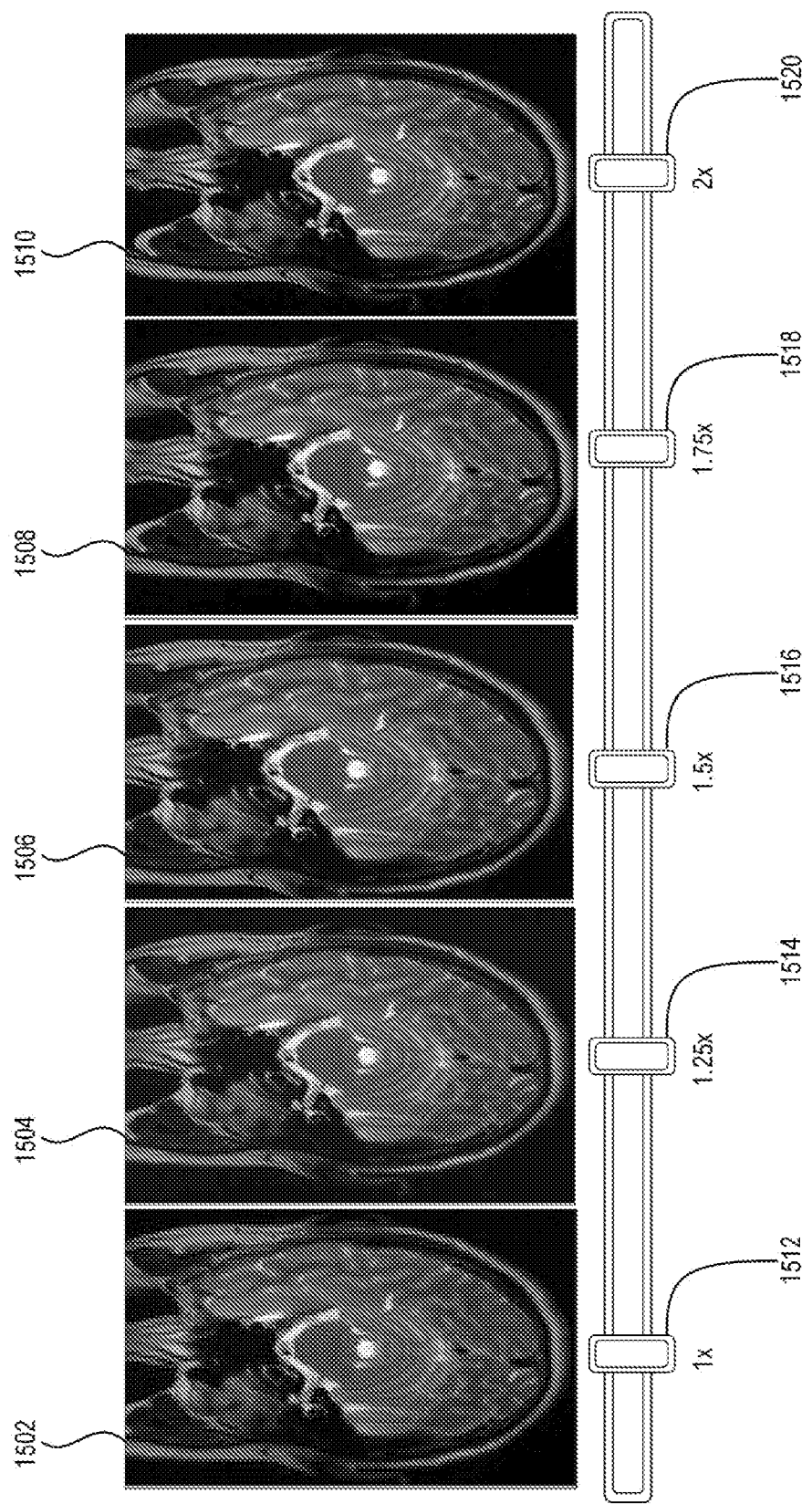
FIG. 15 shows an input image, a plurality of intermediate images, and a super-resolution output image in an example arrangement.

Referring to FIG. 15, an example input image 1502 is shown along with intermediate images and a super-resolution output image generated from the input image. In particular, FIG. 15 shows input image 1502, first intermediate image 1504, second intermediate image 1506, third intermediate image 1508, and super-resolution output image 1510. The intermediate images and output image may be generated from the input image according to the methods described herein.

The input image 1502 has a scale of 1×, as indicated by marker 1512. The scale of each other image is relative to the scale of the input image 1502. Each of the intermediate images has a non-integer scale relative to the input image 1502. The first intermediate image 1504 is generated from the input image 1502 by up-sampling the input image 1502 via a combination of a feature learner and an up-sampling module (e.g., of a deep neural network), similar to the examples described above. The scale of the resulting first intermediate image 1504 is 1.25× (as indicated by marker 1514) as compared to the 1× scale of the input image 1502, resulting in the resolution (e.g., number of voxels) of the first intermediate image 1504 being equal to the resolution of the input image 1502 multiplied by 1.25.

The second intermediate image 1506 is generated from the first intermediate image 1504 by up-sampling the first intermediate image 1504 via a combination of a feature learner and an up-sampling module. The scale of the resulting second intermediate image 1506 is 1.5× (as indicated by marker 1516) as compared to the 1× scale of the input image 1502, resulting in the resolution of the second intermediate image 1506 being equal to the resolution of the input image 1502 multiplied by 1.5.

The third intermediate image 1508 is generated from the second intermediate image 1506 by up-sampling the second intermediate image 1506 via a combination of a feature learner and an up-sampling module. The scale of the resulting third intermediate image 1508 is 1.75× (as indicated by marker 1518) as compared to the 1× scale of the input image 1502, resulting in the resolution of the third intermediate image 1508 being equal to the resolution of the input image 1502 multiplied by 1.75.

The super-resolution output image 1510 is generated from the third intermediate image 1508 up-sampling the third intermediate image 1508 via a combination of a feature learner and an up-sampling module. The scale of the resulting super-resolution output image 1510 is 2× (as indicated by marker 1520) as compared to the 1× scale of the input image 1502, resulting in the resolution of the super-resolution output image being equal to the resolution of the input image 1502 multiplied by 2. However, due to the generation of the intermediate images and the up-sampling and processing via a combination of a feature learner and an up-sampling module as described above for each of the intermediate images, a clarity and contrast of features shown by the super-resolution output image 1510 may be greater than the clarity and contrast of said features shown in the input image 1502.

As a result, an interpretability of the super-resolution output image may be increased, which may increase an ease of evaluation of the super-resolution output image 1510 by an operator of the image processing system (e.g., diagnosis, treatment, etc. of a patient with anatomical features shown by the super-resolution output image 1510 and input image 1502). Additionally, each of the input image 1502, the intermediate images, and the super-resolution output image 1510 may be displayed together by a display device (e.g., similar to, or the same as, the display device 120 described above with reference to FIG. 1) to increase an ease of comparison of the features throughout the images. As one example, the input image 1502, intermediate images, and super-resolution output image 1510 may be displayed side-by-side, similar to the arrangement shown by FIG. 15, and the display may include the markers indicating the relative scale of each image in some examples.

Figure 16:
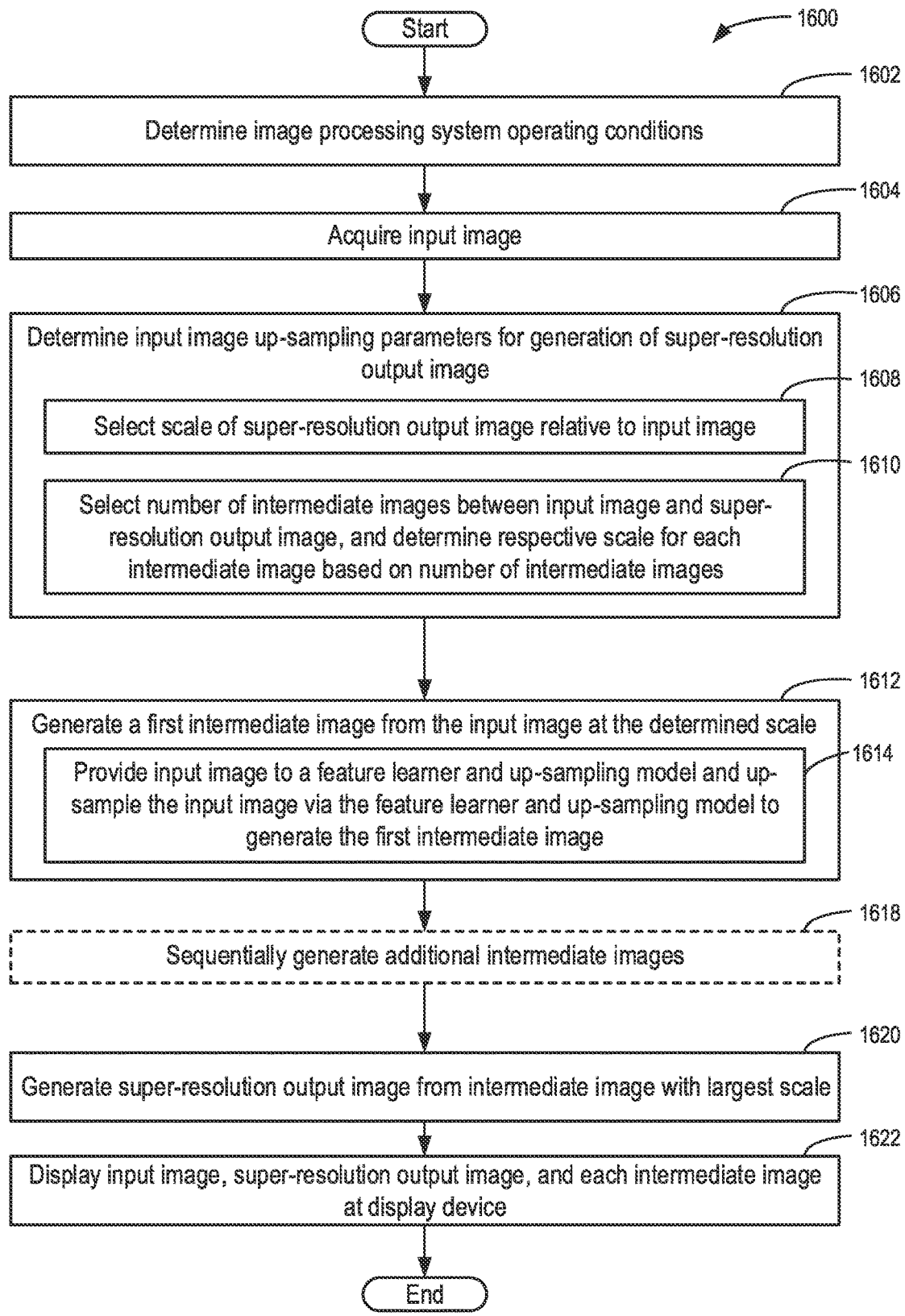
FIG. 16 shows a flowchart illustrating a method for progressive sub-voxel up-sampling of an input image to generate a super-resolution output image.

Referring to FIG. 16, a flowchart illustrating a method 1600 for performing progressive sub-voxel up-sampling of an input image to generate a super-resolution output image is shown. Instructions for carrying out method 1600 and the rest of the methods included herein may be executed by a controller (e.g., image processing device 102 described above with reference to FIG. 1) based on instructions stored on a memory of the controller and in conjunction with signals received from devices such as a user input device (e.g., user input device 130 described above with reference to FIG. 1).

At 1602, the method includes determining image processing system operating conditions. The image processing system may be similar to, or the same as, the image processing system 100 described above with reference to FIG. 1. Determining the image processing system operating conditions may include determining a modality of images provided to the image processing system, determining images stored to a memory of the image processing system, determining images displayed by a display device in communication with the image processing system, etc.

The method continues from 1602 to 1604 where the method includes acquiring an input image. In some examples, the input image may be a medical image generated by a medical imaging system, such as a magnetic resonance imaging (MRI) system, a computed tomography (CT) imaging system, an ultrasound imaging system, etc. Acquiring the input image may include loading the input image to a memory of the image processing system (e.g., communicating with the medical imaging system to load the input image to the memory of the image processing system). In some examples, the image processing system may be integrated directly with the medical imaging system such that acquisition of the input image occurs concurrently with generation of the input image by the medical imaging system. In some examples, the image processing system may be integrated with a different type of imaging system (e.g., a microscope imaging system, camera imaging system, etc.), and the image processing system may acquire the input image concurrently with generation of the input image by the imaging system.

The method continues from 1604 to 1606 where the method includes determining input image up-sampling parameters for generation of a super-resolution output image. Determining the input image up-sampling parameters includes inputting a selection of a scale of the super-resolution output image and a number of intermediate images to be generated in performing the generation of the super-resolution output image, as described below.

The method at 1606 includes, at 1608, selecting a scale of the super-resolution output image relative to the input image. As described above, the scale of the input image is 1×, and the scale of the super-resolution output image is relative to the scale of the input image. Further, the scale of each intermediate image is relative to the scale of the input image. Selecting the scale of the super-resolution output image may include inputting the selection of the desired scale via a user input device, such as the user input device 130 described above with reference to FIG. 1. The user (e.g., operator of the image processing system, such as a clinician) may input the selection of the desired scale of the super-resolution output image for generation of the super-resolution output image from the input image as described below. As one example, the scale of the super-resolution output image may be selected to be 2×, resulting in a super-resolution output image with twice as many voxels as the input image. As another example, the scale of the super-resolution output image may be selected to be 4×, resulting in a super-resolution output image with four times as many voxels as the input image. Other examples are possible.

The method at 1606 includes, at 1610, selecting a number of intermediate images between the input image and the super-resolution output image, and determining a respective scale for each intermediate image based on number of intermediate images. Selecting the number of intermediate images may include inputting the selection of the number of intermediate images via the user input device. The user may input the selection of the number of intermediate images for generation of the super-resolution output image from the input image as described below. As one example, the selected number of intermediate images may be one. As another example, the selected number of intermediate images may be three. Other examples are possible.

The respective scale for each intermediate image is based on the selected number of intermediate images and is further based on the selected scale of the super-resolution output image. The image processing system may determine the scale of each intermediate image responsive to the selection of the desired number of intermediate images by the user. For example, the user may input a selection of one intermediate image, and the user may additionally input a selection of a scale of 2× for the super-resolution output image. As a result, the image processing system may determine the scale of the one intermediate image to be 1.5×, where the scale of the one intermediate image is halfway between the 1× scale of the input image and the selected 2× scale of the super-resolution output image. However, this is just one example. In some examples a non-uniformly distributed resolution for intermediate stages may be used.

As another example, the user may input a selection of three intermediate images, and the user may additionally input a selection of a scale of 2× for the super-resolution output image. As a result, the image processing system may determine the scale of a first intermediate image of the three intermediate images to be 1.25×, a scale of a second intermediate image of the three intermediate images to be 1.5×, and a scale of a third intermediate image of the three intermediate images to be 1.75×. The image processing system determines the respective scale of each intermediate image by calculating the difference between the scale of the input image and the selected scale of the super-resolution output image and calculating scales for the intermediate images spaced apart by equal intervals. In the example in which the selected scale of the super-resolution output image is 2× and the selected number of intermediate images is three, the image processing system calculates three incremental scales between 1× and 2×, namely 1.25×, 1.5×, and 1.75×, as described above. Other examples are possible.

The method continues from 1606 to 1612 where the method includes generating a first intermediate image from the input image at the determined scale.

The method at 1612 includes, at 1614, providing the input image to a feature learner and an up-sampling model and up-sampling the input image via the feature learner and up-sampling model to generate the first intermediate image. Providing the input image to the feature learner and up-sampling model may be similar to, or the same as, the examples described above with reference to FIGS. 2-4 and/or FIGS. 6-8. The feature learner and up-sampling model may be included within a deep neural network trained to generate the first intermediate image from the input image. The deep neural network may be further trained to generate a super-resolution output image from the first intermediate image and/or generate additional intermediate images as described further below.

The feature learner and up-sampling module may be trained by a training module, such as the training module 112 described above with reference to FIG. 1. The training of the feature learner and up-sampling module by the training module may be similar to, or the same as, the training described above with reference to FIG. 2, in some examples.

A resolution of the first intermediate image is a multiple of a resolution of the input image, higher than the resolution of the input image, and can be any positive real value and not necessarily an integer value. For example, a scale of the input image may be 1×, and a scale of the first intermediate image may be 1.5× (where the resolution of the first intermediate image is equal to the resolution of the input image multiplied by 1.5). The feature learner and up-sampling model may be trained in particular to up-sample the input image from the 1× scale to the scale of the first intermediate image during generation of the first intermediate image. The feature learner and up-sampling model may be further trained to up-sample the first intermediate image from the scale of the first intermediate image to the scale of the super-resolution output image during generation of the super-resolution output image, as described further below.

The method may continue from 1612 to 1618 where the method includes sequentially generating additional intermediate images. For example, during conditions in which the user inputs a selection of more than one intermediate image to be generated during the generation of the super-resolution output image from the input image, the image processing system generates the additional intermediate images following the first intermediate image in sequential order. As one example, the user may input a selection of three intermediate images to be generated during the generation of the super-resolution output image from the input image. The image processing system generates the first intermediate image as described above, and the first intermediate image is then up-sampled via the feature learner and up-sampling model as described above with reference to the input image, resulting in the generation of the second intermediate image. The up-sampling process is repeated with the second intermediate image to generate the third intermediate image, where the weights and/or parameters of the up-sampling model may be different for generating the first intermediate image from the input image as compared to the weights and/or parameters for generating the second intermediate image from the first intermediate image, the weights and/or parameters for generating the third intermediate image from the second intermediate image, and/or the weights and/or parameters for generating the super-resolution output image from the third intermediate image.

The resolution of each intermediate image generated at 1618 is a multiple of the resolution of the input image, higher than the resolution of the input image, and can be any positive real value and not necessarily an integer value, similar to the examples described above. As one example, the resolution of the first intermediate image may be equal to the resolution of the input image multiplied by 1.25, the resolution of the second intermediate image may be equal to the resolution of the input image multiplied by 1.5, and the resolution of the third intermediate image may be equal to the resolution of the input image multiplied by 1.75. Other examples are possible, where the resolution of each intermediate image is a multiple of the resolution of the input image, higher than the resolution of the input image, and can be any positive real value and not necessarily an integer value.

The method may continue from 1618 to 1620, or if the number of intermediate images selected is one at 1610, the method may continue from 1612 to 1620 without sequentially generating the additional intermediate images at 1618.

The method at 1620 includes generating the super-resolution output image from the intermediate image with the largest scale. Generating the super-resolution output image includes up-sampling the intermediate image via the feature learner and up-sampling model, similar to the up-sampling described above. In the example in which the user selects the single intermediate image to be generated during the generation of the super-resolution output image from the input image, the single intermediate image is up-sampled via the feature learner and up-sampling model to generate the super-resolution output image. In the example in which the user selects three intermediate images to be generated during the generation of the super-resolution, the scale of the first intermediate image may be 1.25x, the scale of the second intermediate image may be 1.5x, and the scale of the third intermediate image may be 1.75x as described above. In the example, the third intermediate image has the largest scale (relative to the first intermediate image and second intermediate image) and is up-sampled via the feature learner and up-sampling model as described above to generate the super-resolution output image.

The method continues from 1620 to 1622 where the method includes displaying the input image, the super-resolution output image, and each intermediate image at a display device. The display device may be similar to, or the same as, the display device 120 described above with reference to FIG. 1. In one example, the input image, super-resolution output image, and each intermediate image may be displayed in an arrangement similar to the arrangement shown by FIG. 15 and described above. By displaying the input image, the super-resolution output image, and each of the intermediate images together, the user may more easily compare the features shown by each image, and a confidence of identification of the features may be increased.

Figure 17:
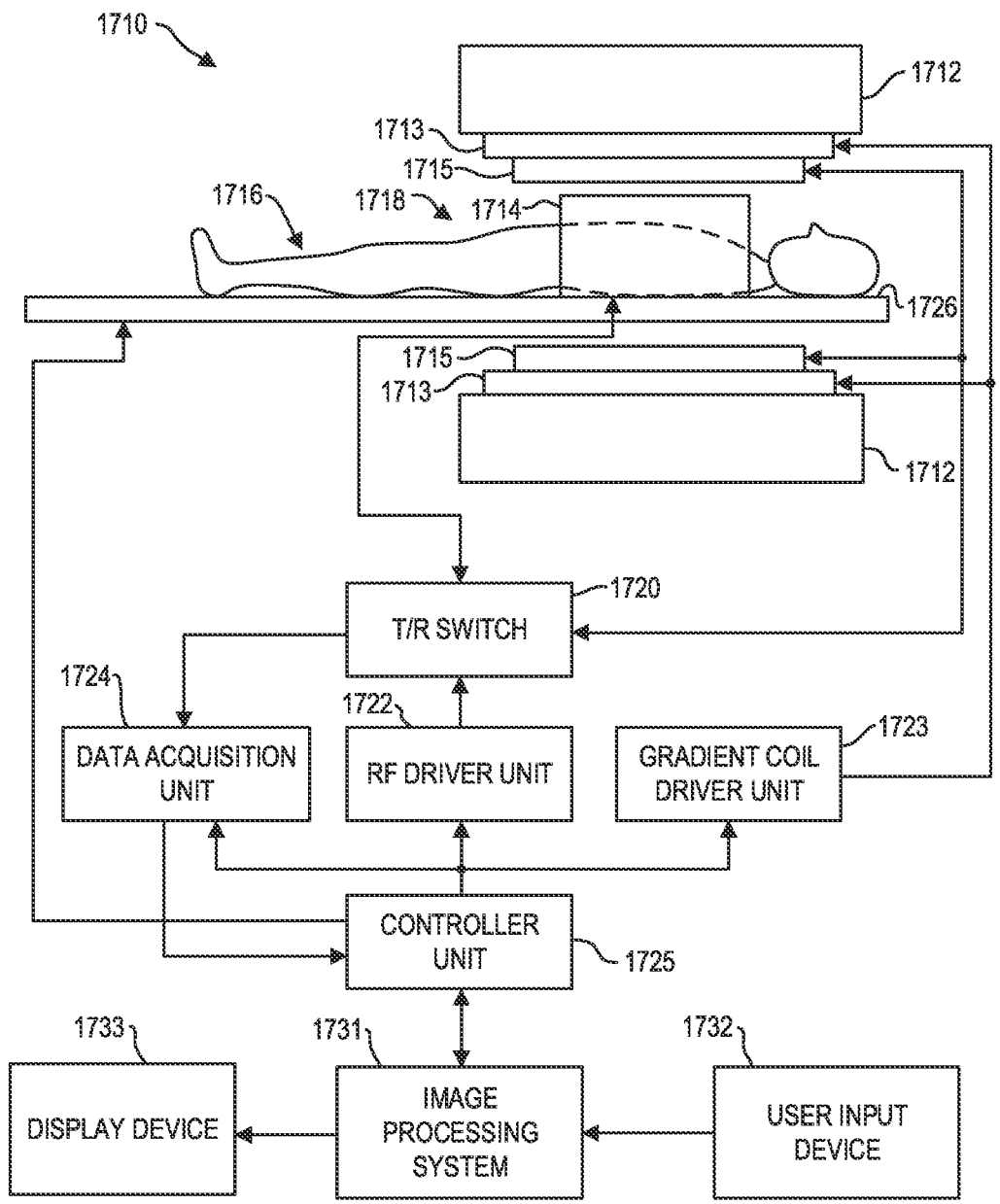
FIG. 17 schematically shows an imaging system that may acquire images for progressive sub-voxel up-sampling according to an embodiment.

Referring to FIG. 17, a magnetic resonance imaging (MRI) apparatus 1710 is shown that includes a magnetostatic field magnet unit 1712, a gradient coil unit 1713, an RF coil unit 1714, an RF body or volume coil unit 1715, a transmit/receive (T/R) switch 1720, an RF driver unit 1722, a gradient coil driver unit 1723, a data acquisition unit 1724, a controller unit 1725, a patient table or bed 1726, an image processing system 1731, an operating console unit 1732, and a display unit 1733.

The MRI apparatus 1710 is one example of a medical imaging system that may be utilized in the performance of the methods described above. For example, the MRI apparatus 1710 may acquire images of a subject (e.g., a patient), and the images acquired by the MRI apparatus 1710 may be acquired as input images according to the method 1600 described above with reference to FIG. 16. As one example, the MRI apparatus 1710 may acquire images of the subject, and the images of the subject may be transmitted to an image processing system (e.g., image processing system 100 described above with reference to FIG. 1) external to the MRI apparatus. The image processing system may then perform progressive sub-voxel up-sampling of the images transmitted to the image processing system by the MRI apparatus 1710 according to the methods described herein (e.g., an image transmitted to the image processing system by the MRI apparatus 1710 may be acquired by the image processing system as an input image as described at 1604 of method 1600).

As another example, the imaging processing system configured to perform progressive sub-voxel up-sampling of images acquired by the MRI apparatus 1710 may be integrated directly with the MRI apparatus 1710, and the progressive sub-voxel up-sampling of the images may be performed as the images are acquired by the MRI apparatus 1710 (e.g., concurrently with imaging of the subject by the MRI apparatus 1710) or following acquisition of the images by the MRI apparatus 1710 (e.g., the progressive sub-voxel up-sampling of images may be performed using images stored to memory of the MRI apparatus 1710). For example, the imaging processing system may be image processing system 1731 shown by FIG. 17 and may be similar to, or the same as, the image processing system 100 shown by FIG. 1 and described above.

The images of the subject (e.g., medical images) acquired by the MRI apparatus 1710 include three-dimensional image data, e.g., voxels. According to the methods described herein, voxels included by an image may be sub-divided into sub-voxels, where each sub-voxel is three-dimensional image data representing a portion of a corresponding voxel. In some examples, a size of the voxels and/or sub-voxels may be based on an anatomy imaged by the MRI apparatus 1710. As one example, the size of the voxels and/or sub-voxels may be selected to provide a desired number of voxels and/or sub-voxels to represent the anatomy of interest of the imaged subject (e.g., larger voxel and/or sub-voxel sizes may be selected for imaging of relatively large anatomical structures, and smaller voxel and/or sub-voxel sizes may be selected for imaging of relatively smaller anatomical structures). Up-sampling an input resolution having a first resolution to generate an intermediate image having a second resolution that is a multiple of the first resolution, higher than the first resolution, and can be any positive real value and not necessarily an integer value, according to the methods described herein may include generating additional voxels and/or sub-voxels included by the intermediate image based on the voxels and/or sub-voxels included by the input image. For example, up-sampling an input image from a scale of 1× to generate an intermediate image with a scale of 1.25× may include generating the additional voxels of the intermediate image from voxel and/or sub-voxel image data of the input image.

In some embodiments, the images acquired as input images by the image processing system may include multiple slices. For example, the MRI apparatus 1710 may image a subject by acquiring a plurality of images (which may be referred to herein as slices) of the subject taken along different parallel imaging planes, and the plurality of images may be combined by the image processing system to form a three-dimensional image of the subject including voxel and sub-voxel image data. The progressive sub-voxel up-sampling described herein may be performed using the three-dimensional image assembled from the plurality of slices as an input image. In some embodiments, multiple images including three-dimensional image data may be acquired by imaging the subject via the MRI apparatus 1710 at different depths of the anatomy of interest, and the multiple three-dimensional images may be combined to form a single three-dimensional image. The progressive sub-voxel up-sampling described herein may then be performed using the combined three-dimensional image as an input image. Other examples are possible.

In some embodiments, the RF coil unit 1714 is a surface coil, which is a local coil typically placed proximate to the anatomy of interest of a subject 1716. Herein, the RF body coil unit 1715 is a transmit coil that transmits RF signals, and the local surface RF coil unit 1714 receives the MR signals. As such, the transmit body coil (e.g., RF body coil unit 1715) and the surface receive coil (e.g., RF coil unit 1714) are separate but electromagnetically coupled components. The MRI apparatus 1710 transmits electromagnetic pulse signals to the subject 1716 placed in an imaging space 1718 with a static magnetic field formed to perform a scan for obtaining magnetic resonance signals from the subject 1716. One or more images of the subject 1716 can be reconstructed based on the magnetic resonance signals thus obtained by the scan.

The magnetostatic field magnet unit 1712 includes, for example, an annular superconducting magnet, which is mounted within a toroidal vacuum vessel. The magnet defines a cylindrical space surrounding the subject 1716 and generates a constant primary magnetostatic field $B_0$.

The MRI apparatus 1710 also includes a gradient coil unit 1713 that forms a gradient magnetic field in the imaging space 1718 so as to provide the magnetic resonance signals received by the RF coil arrays with three-dimensional positional information. The gradient coil unit 1713 may include three gradient coil systems, each of which generates a gradient magnetic field along one of three spatial axes perpendicular to each other, and generates a gradient field in each of a frequency encoding direction, a phase encoding direction, and a slice selection direction in accordance with the imaging condition. More specifically, the gradient coil unit 1713 applies a gradient field in the slice selection direction (or scan direction) of the subject 1716, to select the slice; and the RF body coil unit 1715 or the local RF coil arrays may transmit an RF pulse to a selected slice of the subject 1716. The gradient coil unit 1713 also applies a gradient field in the phase encoding direction of the subject 1716 to phase encode the magnetic resonance signals from the slice excited by the RF pulse. The gradient coil unit 1713 then applies a gradient field in the frequency encoding direction of the subject 1716 to frequency encode the magnetic resonance signals from the slice excited by the RF pulse.

The RF coil unit 1714 is disposed, for example, to enclose the region to be imaged of the subject 1716. In some examples, the RF coil unit 1714 may be referred to as the surface coil or the receive coil. In the static magnetic field space or imaging space 1718 where a static magnetic field $B_0$ is formed by the magnetostatic field magnet unit 1712, the RF body coil unit 1715 transmits, based on a control signal from the controller unit 1725, an RF pulse that is an electromagnet wave to the subject 1716 and thereby generates a high-frequency magnetic field $B_1$. This excites a spin of protons in the slice to be imaged of the subject 1716. The RF coil unit 1714 receives, as a magnetic resonance signal, the electromagnetic wave generated when the proton spin thus excited in the slice to be imaged of the subject 1716 returns into alignment with the initial magnetization vector. In some embodiments, the RF coil unit 1714 may transmit the RF pulse and receive the MR signal. In other embodiments, the RF coil unit 1714 may only be used for receiving the MR signals, but not transmitting the RF pulse.

The RF body coil unit 1715 is disposed, for example, to enclose the imaging space 1718, and produces RF magnetic field pulses orthogonal to the main magnetic field $B_0$ produced by the magnetostatic field magnet unit 1712 within the imaging space 1718 to excite the nuclei. In contrast to the RF coil unit 1714, which may be disconnected from the MRI apparatus 1710 and replaced with another RF coil unit, the RF body coil unit 1715 is fixedly attached and connected to the MRI apparatus 1710. Furthermore, whereas local coils such as the RF coil unit 1714 can transmit to or receive signals from only a localized region of the subject 1716, the RF body coil unit 1715 generally has a larger coverage area. The RF body coil unit 1715 may be used to transmit or receive signals to the whole body of the subject 1716, for example. Using receive-only local coils and transmit body coils provides a uniform RF excitation and good image uniformity at the expense of high RF power deposited in the subject. For a transmit-receive local coil, the local coil provides the RF excitation to the region of interest and receives the MR signal, thereby decreasing the RF power deposited in the subject. It should be appreciated that the particular use of the RF coil unit 1714 and/or the RF body coil unit 1715 depends on the imaging application.

The T/R switch 1720 can selectively electrically connect the RF body coil unit 1715 to the data acquisition unit 1724 when operating in receive mode, and to the RF driver unit 1722 when operating in transmit mode. Similarly, the T/R switch 1720 can selectively electrically connect the RF coil unit 1714 to the data acquisition unit 1724 when the RF coil unit 1714 operates in receive mode, and to the RF driver unit 1722 when operating in transmit mode. When the RF coil unit 1714 and the RF body coil unit 1715 are both used in a single scan, for example if the RF coil unit 1714 is configured to receive MR signals and the RF body coil unit 1715 is configured to transmit RF signals, then the T/R switch 1720 may direct control signals from the RF driver unit 1722 to the RF body coil unit 1715 while directing received MR signals from the RF coil unit 1714 to the data acquisition unit 1724. The coils of the RF body coil unit 1715 may be configured to operate in a transmit-only mode or a transmit-receive mode. The coils of the local RF coil unit 1714 may be configured to operate in a transmit-receive mode or a receive-only mode.

The RF driver unit 1722 includes a gate modulator (not shown), an RF power amplifier (not shown), and an RF oscillator (not shown) that are used to drive the RF coils (e.g., RF body coil unit 1715) and form a high-frequency magnetic field in the imaging space 1718. The RF driver unit 1722 modulates, based on a control signal from the controller unit 1725 and using the gate modulator, the RF signal received from the RF oscillator into a signal of predetermined timing having a predetermined envelope. The RF signal modulated by the gate modulator is amplified by the RF power amplifier and then output to the RF body coil unit 1715.

The gradient coil driver unit 1723 drives the gradient coil unit 1713 based on a control signal from the controller unit 1725 and thereby generates a gradient magnetic field in the imaging space 1718. The gradient coil driver unit 1723 includes three systems of driver circuits (not shown) corresponding to the three gradient coil systems included in the gradient coil unit 1713.

The data acquisition unit 1724 includes a pre-amplifier (not shown), a phase detector (not shown), and an analog/digital converter (not shown) used to acquire the magnetic resonance signals received by the RF coil unit 1714. In the data acquisition unit 1724, the phase detector phase detects, using the output from the RF oscillator of the RF driver unit 1722 as a reference signal, the magnetic resonance signals received from the RF coil unit 1714 and amplified by the pre-amplifier, and outputs the phase-detected analog magnetic resonance signals to the analog/digital converter for conversion into digital signals. The digital signals thus obtained are output to the image processing system 1731.

The MRI apparatus 1710 includes table 1726 for placing the subject 1716 thereon. The subject 1716 may be moved inside and outside the imaging space 1718 by moving the table 1726 based on control signals from the controller unit 1725.

The controller unit 1725 includes a computer and a recording medium on which a program to be executed by the computer is recorded. The program when executed by the computer causes various parts of the apparatus to carry out operations corresponding to pre-determined scanning. The recording medium may comprise, for example, a ROM, flexible disk, hard disk, optical disk, magneto-optical disk, CD-ROM, or non-volatile memory card. The controller unit 1725 is connected to the operating console unit 1732 and processes the operation signals input to the operating console unit 1732 and furthermore controls the table 1726, RF driver unit 1722, gradient coil driver unit 1723, and data acquisition unit 1724 by outputting control signals to them. The controller unit 1725 also controls, to obtain a desired image, the image processing system 1731 and the display unit 1733 based on operation signals received from the operating console unit 1732.

The operating console unit 1732 includes user input devices such as a touchscreen, keyboard and a mouse. The operating console unit 1732 is used by an operator, for example, to input such data as an imaging protocol and to set a region where an imaging sequence is to be executed. The data about the imaging protocol and the imaging sequence execution region are output to the controller unit 1725.

The image processing system 1731 includes a computer and a recording medium on which a program to be executed by the computer to perform predetermined data processing is recorded. The image processing system 1731 is connected to the controller unit 1725 and performs data processing based on control signals received from the controller unit 1725. image processing system 1731 is also connected to the data acquisition unit 1724 and generates spectrum data by applying various image processing operations to the magnetic resonance signals output from the data acquisition unit 1724.

The display unit 1733 includes a display device and displays an image on the display screen of the display device based on control signals received from the controller unit 1725. The display unit 1733 displays, for example, an image regarding an input item about which the operator inputs operation data from the operating console unit 1732. The display unit 1733 also displays a two-dimensional (2D) slice image or three-dimensional (3D) image of the subject 1716 generated by the image processing system 1731.

Though a MRI system is described by way of example, it should be understood that the present techniques may also be useful when applied to images acquired using other imaging modalities, such as CT, tomosynthesis, PET, C-arm angiography, and so forth. The present discussion of an MRI imaging modality is provided merely as an example of one suitable imaging modality.

The technical effect of progressive sub-voxel up-sampling to generate super-resolution output images is to increase the image quality of the output image relative to the input image.

The disclosure also provides support for a method, comprising: progressively up-sampling an input image to generate a super-resolution output image by: generating a first intermediate image directly from the input image by providing the input image to a deep neural network, where a resolution of the first intermediate image is a non-integer multiple of a resolution of the input image, generating the super-resolution output image based on the first intermediate image, the super-resolution output image having a resolution higher than each of the resolution of the first intermediate image and the resolution of the input image, and displaying the super-resolution output image via a display device and/or storing the super-resolution output image to a computer memory. In a first example of the method, generating the super-resolution output image based on the first intermediate image includes providing the first intermediate image to the deep neural network. In a second example of the method, optionally including the first example, generating the super-resolution output image based on the first intermediate image includes: generating a second intermediate image directly from the first intermediate image by providing the first intermediate image to the deep neural network, where a resolution of the second intermediate image is a non-integer multiple of the resolution of the input image, and generating the super-resolution output image based on the second intermediate image. In a third example of the method, optionally including one or both of the first and second examples, generating the super-resolution output image based on the second intermediate image includes: providing the second intermediate image to the deep neural network. In a fourth example of the method, optionally including one or more or each of the first through third examples, generating the super-resolution output image based on the second intermediate image includes: generating a third intermediate image directly from the second intermediate image by providing the second intermediate image to the deep neural network, where a resolution of the third intermediate image is a non-integer multiple of the resolution of the input image, and generating the super-resolution output image based on the third intermediate image. In a fifth example of the method, optionally including one or more or each of the first through fourth examples, the first intermediate image is one of a plurality of intermediate images based on the input image. In a sixth example of the method, optionally including one or more or each of the first through fifth examples, each intermediate image of the plurality of intermediate images has a respective resolution, and each respective resolution is greater than the resolution of the input image. In a seventh example of the method, optionally including one or more or each of the first through sixth examples, each respective resolution is a different non-integer multiple of the resolution of the input image relative to each other respective resolution. In a eighth example of the method, optionally including one or more or each of the first through seventh examples, the plurality of intermediate images includes the first intermediate image, a second intermediate image based on the first intermediate image, and a third intermediate image based on the second intermediate image. In a ninth example of the method, optionally including one or more or each of the first through eighth examples, the respective resolution of the first intermediate image is equal to the resolution of the input image multiplied by an amount greater than 1.0 and less than 1.5, and the respective resolution of the third intermediate image is equal to the resolution of the input image multiplied by an amount greater than 1.5 and less than 2.0. In a tenth example of the method, optionally including one or more or each of the first through ninth examples, the method further comprises: displaying the input image, the first intermediate image, and the super-resolution output image concurrently via the display device. In a eleventh example of the method, optionally including one or more or each of the first through tenth examples, the deep neural network is a convolutional neural network.

The disclosure also provides support for a method, comprising: acquiring a medical image, generating a first intermediate image from the medical image via an up-sampling model trained on images acquired with an imaging modality of the medical image, where a resolution of the first intermediate image is a non-integer multiple of a resolution of the medical image, and generating a super-resolution output image based on the first intermediate image via the up-sampling model. In a first example of the method, generating the super-resolution output image based on the first intermediate image includes zero-padding a k-space of image data of the first intermediate image and providing the first intermediate image to the up-sampling model. In a second example of the method, optionally including the first example, generating the super-resolution output image based on the first intermediate image includes generating a second intermediate image from the first intermediate image by zero-padding a k-space of image data of the first intermediate image and providing the first intermediate image with the zero-padded k-space image data to the up-sampling model, and zero-padding a k-space of image data of the second intermediate image and providing the second intermediate image with the zero-padded k-space image data to the up-sampling model to generate the super-resolution output image. In a third example of the method, optionally including one or both of the first and second examples, a resolution of the second intermediate image is a non-integer multiple of the resolution of the medical image and is greater than the resolution of the first intermediate image. In a fourth example of the method, optionally including one or more or each of the first through third examples, the imaging modality is magnetic resonance imaging (MRI).

The disclosure also provides support for a system, comprising: a memory storing a deep neural network, and instructions, and a processor, wherein the processor is communicably coupled to the memory, and when executing the instructions, is configured to: generate a first intermediate image directly from an input image by providing the input image to the deep neural network, where a resolution of the first intermediate image is a non-integer multiple of a resolution of the input image, and generate a super-resolution output image based on the first intermediate image, the super-resolution output image having a resolution higher than each of the resolution of the first intermediate image and the resolution of the input image. In a first example of the system, the system further comprises: instructions stored in the memory that when executed, cause the processor to: up-sample the first intermediate image via the deep neural network. In a second example of the system, optionally including the first example, the system further comprises: instructions stored in the memory that when executed, cause the processor to: zero-pad a k-space of image data of the first intermediate image prior to generating the super-resolution output image based on the first intermediate image.

The disclosure also provides support for a method, comprising: progressively up-sampling an input image to generate a super-resolution output image by: generating N intermediate images based on the input image, where N is equal to at least one, including a first intermediate image by providing the input image to a deep neural network, where a resolution of the first intermediate image is a multiple of a resolution of the input image, higher than the resolution of the input image, and can be any positive real value and not necessarily an integer value, generating the super-resolution output image based on the N intermediate images, the super-resolution output image having a resolution higher than a respective resolution of each intermediate image of the N intermediate images and the resolution of the input image, and displaying the super-resolution output image via a display device and/or storing the super-resolution output image to a computer memory. In a first example of the method, generating the super-resolution output image based on the first intermediate image includes providing the first intermediate image to the deep neural network. In a second example of the method, optionally including the first example, generating the super-resolution output image based on the N intermediate images includes: generating a second intermediate image directly from the first intermediate image by providing the first intermediate image to the deep neural network, where a resolution of the second intermediate image is a multiple of the resolution of the input image, higher than the resolution of the input image, and can be any positive real value and not necessarily an integer value, and generating the super-resolution output image based on the second intermediate image. In a third example of the method, optionally including one or both of the first and second examples, generating the super-resolution output image based on the second intermediate image includes: providing the second intermediate image to the deep neural network. In a fourth example of the method, optionally including one or more or each of the first through third examples, generating the super-resolution output image based on the second intermediate image includes: generating a third intermediate image directly from the second intermediate image by providing the second intermediate image to the deep neural network, where a resolution of the third intermediate image is a multiple of the resolution of the input image, higher than the resolution of the input image, and can be any positive real value and not necessarily an integer value, and generating the super-resolution output image based on the third intermediate image. In a fifth example of the method, optionally including one or more or each of the first through fourth examples, the first intermediate image is first in a sequence of the N intermediate images. In a sixth example of the method, optionally including one or more or each of the first through fifth examples, each intermediate image of the N intermediate images has a respective resolution higher than each preceding intermediate image of the N intermediate images in the sequence of the N intermediate images. In a seventh example of the method, optionally including one or more or each of the first through sixth examples, a respective resolution of each intermediate image of the N intermediate images is a different multiple of the resolution of the input image relative to the respective resolution of each other intermediate image of the N intermediate images. In a eighth example of the method, optionally including one or more or each of the first through seventh examples, the N intermediate images includes the first intermediate image, a second intermediate image based on the first intermediate image, and a third intermediate image based on the second intermediate image. In a ninth example of the method, optionally including one or more or each of the first through eighth examples, the respective resolution of the first intermediate image is equal to the resolution of the input image multiplied by an amount within a first range of positive real values and is not necessarily an integer value, and the respective resolution of the third intermediate image is equal to the resolution of the input image multiplied by an amount within a second range of positive real values and is not necessarily an integer value. In a tenth example of the method, optionally including one or more or each of the first through ninth examples, the method further comprises: displaying the input image, the N intermediate images, and the super-resolution output image concurrently via the display device. In a eleventh example of the method, optionally including one or more or each of the first through tenth examples, the deep neural network is a convolutional neural network.

The disclosure also provides support for a method, comprising: acquiring a medical image, generating N intermediate images based on the medical image, where N is equal to at least one, including a first intermediate image via a feature learner and an up-sampling model trained on images acquired with an imaging modality of the medical image, where a resolution of the first intermediate image is a multiple of a resolution of the medical image, higher than the resolution of the medical image, and can be any positive real value and not necessarily an integer value, and generating a super-resolution output image based on the N intermediate images via the feature learner and the up-sampling model. In a first example of the method, the imaging modality is magnetic resonance imaging (MRI). In a second example of the method, optionally including the first example, generating the super-resolution output image based on the N intermediate images includes zero-padding a k-space of MR image data of the first intermediate image and providing the first intermediate image to the feature learner and the up-sampling model. In a third example of the method, optionally including one or both of the first and second examples, generating the super-resolution output image based on the N intermediate images includes generating a second intermediate image from the first intermediate image by providing the first intermediate image to the feature learner and the up-sampling model, where a k-space of image data of the first intermediate image is zero-padded by the up-sampling model, and providing the second intermediate image to the feature learner and the up-sampling model to generate the super-resolution output image. In a fourth example of the method, optionally including one or more or each of the first through third examples, a resolution of the second intermediate image is a multiple of the resolution of the medical image, is greater than the resolution of the first intermediate image, and can be any positive real value and not necessarily an integer value.

The disclosure also provides support for a system, comprising: a memory storing a deep neural network, and instructions, and a processor, wherein the processor is communicably coupled to the memory, and when executing the instructions, is configured to: generate N intermediate images based on an input image, where N is equal to at least one, including a first intermediate image by providing the input image to the deep neural network, where a resolution of the first intermediate image is a multiple of a resolution of the input image, higher than the resolution of the input image, and can be any positive real value and not necessarily an integer value, and generate a super-resolution output image based on the N intermediate images, the super-resolution output image having a resolution higher than a respective resolution of each intermediate image of the N intermediate images and the resolution of the input image. In a first example of the system, the system further comprises: instructions stored in the memory that when executed, cause the processor to: up-sample the first intermediate image via the deep neural network. In a second example of the system, optionally including the first example, the system further comprises: instructions stored in the memory that when executed, cause the processor to: zero-pad a k-space of image data of the first intermediate image prior to generating the super-resolution output image based on the first intermediate image.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   training a deep neural network, wherein training the deep neural network comprises:
      generating, using a ground truth image having a first resolution, a second image having a second resolution, wherein the first resolution is higher than the second resolution;
      predicting, using the second image, a third image at a third resolution higher than the second resolution; and
      computing loss, wherein computing loss comprises comparing the third image to the ground truth image or an image generated from the ground truth image; and
   progressively up-sampling an input image to generate a super-resolution output image by:
      generating N intermediate images based on the input image, where N is equal to at least one, including a first intermediate image by providing the input image to the trained deep neural network, where a resolution of the first intermediate image is a multiple of a resolution of the input image, higher than the resolution of the input image, and can be any positive real value and not necessarily an integer value;
      generating the super-resolution output image based on the N intermediate images, the super-resolution output image having a resolution higher than a respective resolution of each intermediate image of the N intermediate images and the resolution of the input image; and
      displaying the super-resolution output image via a display device and/or storing the super-resolution output image to a computer memory.

2. The method of claim 1, wherein generating the super-resolution output image based on the first intermediate image includes providing the first intermediate image to the trained deep neural network; and wherein training the deep neural network further comprises:
   generating a plurality of images comprising the second image and a fourth image, wherein the fourth image has a fourth resolution between the second resolution and the first resolution, and
   predicting, using the fourth image, a fifth image having the first resolution;
   wherein computing loss comprises comparing the third image to the fourth image and comparing the fifth image to the ground truth image.

3. The method of claim 1, wherein generating the super-resolution output image based on the N intermediate images includes:
   generating a second intermediate image directly from the first intermediate image by providing the first intermediate image to the deep neural network, where a resolution of the second intermediate image is a multiple of the resolution of the input image, higher than the resolution of the input image, and can be any positive real value and not necessarily an integer value; and
   generating the super-resolution output image based on the second intermediate image.

4. The method of claim 3, wherein generating the super-resolution output image based on the second intermediate image includes:
   providing the second intermediate image to the deep neural network.

5. The method of claim 3, wherein generating the super-resolution output image based on the second intermediate image includes:
   generating a third intermediate image directly from the second intermediate image by providing the second intermediate image to the deep neural network, where a resolution of the third intermediate image is a multiple of the resolution of the input image, higher than the resolution of the input image, and can be any positive real value and not necessarily an integer value; and
   generating the super-resolution output image based on the third intermediate image.

6. The method of claim 1, wherein the first intermediate image is first in a sequence of the N intermediate images.

7. The method of claim 6, wherein each intermediate image of the N intermediate images has a respective resolution higher than each preceding intermediate image of the N intermediate images in the sequence of the N intermediate images.

8. The method of claim 6, wherein a respective resolution of each intermediate image of the N intermediate images is a different multiple of the resolution of the input image relative to the respective resolution of each other intermediate image of the N intermediate images.

9. The method of claim 8, wherein the N intermediate images include the first intermediate image, a second intermediate image based on the first intermediate image, and a third intermediate image based on the second intermediate image.

10. The method of claim 9, wherein the respective resolution of the first intermediate image is equal to the resolution of the input image multiplied by an amount within a first range of positive real values and is not necessarily an integer value, and the respective resolution of the third intermediate image is equal to the resolution of the input image multiplied by an amount within a second range of positive real values and is not necessarily an integer value.

11. The method of claim 1, further comprising displaying the input image, the N intermediate images, and the super-resolution output image concurrently via the display device.

12. The method of claim 1, wherein the deep neural network is a convolutional neural network.

13. A method, comprising:
   acquiring a medical image;
   generating N intermediate images based on the medical image, where N is equal to at least one, including a first intermediate image via a feature learner and an up-sampling model trained on images acquired with an imaging modality of the medical image, where a resolution of the first intermediate image is a multiple of a resolution of the medical image, higher than the resolution of the medical image, and can be any positive real value and not necessarily an integer value;
   generating a super-resolution output image based on the N intermediate images via the feature learner and the up-sampling model; and displaying the medical image, the N intermediate images, and the super-resolution output image side-by-side via a display device, wherein the display device includes markers indicating the relative scale of each image, and wherein displaying the medical image, the N intermediate images, and the super-resolution output image side-by-side comprises displaying the N intermediate images in between the medical image and the super-resolution output image on the display device.

14. The method of claim 13, wherein the imaging modality is magnetic resonance imaging (MRI).

15. The method of claim 14, wherein generating the super-resolution output image based on the N intermediate images includes zero-padding a k-space of MR image data of the first intermediate image and providing the first intermediate image to the feature learner and the up-sampling model.

16. The method of claim 14, wherein generating the super-resolution output image based on the N intermediate images includes generating a second intermediate image from the first intermediate image by providing the first intermediate image to the feature learner and the up-sampling model, where a k-space of image data of the first intermediate image is zero-padded by the up-sampling model, and providing the second intermediate image to the feature learner and the up-sampling model to generate the super-resolution output image.

17. The method of claim 16, wherein a resolution of the second intermediate image is a multiple of the resolution of the medical image, is greater than the resolution of the first intermediate image, and can be any positive real value and not necessarily an integer value.

18. A system, comprising:
a memory storing a deep neural network and instructions, wherein the deep neural network is trained by processing a high-resolution ground truth image to generate a plurality of lower-resolution intermediate images and a low-resolution input image having a resolution lower than each of the plurality of lower-resolution intermediate images, inputting the low-resolution input image into the deep neural network, predicting output images, and comparing each of the output images to the high-resolution ground truth image or an image of the lower-resolution intermediate images to compute loss; and
a processor, wherein the processor is communicably coupled to the memory, and when executing the instructions, is configured to:
generate N intermediate images based on an input image, where N is equal to at least one, including a first intermediate image by providing the input image to the deep neural network, where a resolution of the first intermediate image is a multiple of a resolution of the input image, higher than the resolution of the input image, and can be any positive real value and not necessarily an integer value; and
generate a super-resolution output image based on the N intermediate images, the super-resolution output image having a resolution higher than a respective resolution of each intermediate image of the N intermediate images and the resolution of the input image.

19. The system of claim 18, further comprising instructions stored in the memory that when executed, cause the processor to:
up-sample the first intermediate image via the deep neural network.

20. The system of claim 18, further comprising instructions stored in the memory that when executed, cause the processor to:
zero-pad a k-space of image data of the first intermediate image prior to generating the super-resolution output image based on the first intermediate image.

* * * * *